US011850021B2

(12) United States Patent
Chui et al.

(10) Patent No.: US 11,850,021 B2
(45) Date of Patent: *Dec. 26, 2023

(54) DYNAMIC SELF-LEARNING MEDICAL IMAGE METHOD AND SYSTEM

(71) Applicant: HOLOGIC, INC., Marlborough, MA (US)

(72) Inventors: Haili Chui, Fremont, CA (US); Zhenxue Jing, Chadds Ford, PA (US)

(73) Assignee: Hologic, Inc., Marlborough, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/847,796

(22) Filed: Jun. 23, 2022

(65) Prior Publication Data

US 2023/0033601 A1 Feb. 2, 2023

Related U.S. Application Data

(63) Continuation of application No. 16/623,372, filed as application No. PCT/US2018/035331 on May 31, 2018, now Pat. No. 11,403,483.

(Continued)

(51) Int. Cl.
G06K 9/62 (2022.01)
A61B 5/00 (2006.01)
(Continued)

(52) U.S. Cl.
CPC .......... *A61B 5/0033* (2013.01); *G06F 18/214* (2023.01); *G06F 18/217* (2023.01);
(Continued)

(58) Field of Classification Search
CPC ... A61B 5/0033; A61B 8/0825; A61B 8/5223; A61B 8/565; A61B 6/502; A61B 6/563;
(Continued)

(56) References Cited

U.S. PATENT DOCUMENTS 3,502,878 A 3/1970 Stewart
3,863,073 A 1/1975 Wagner
(Continued)

FOREIGN PATENT DOCUMENTS

AU 2014339982 4/2015
CN 1846622 10/2006
(Continued)

OTHER PUBLICATIONS

"Filtered Back Projection", (Nygren), published May 8, 2007, URL: http://web.archive.org/web/19991010131715/http://www.owlnet.rice.edu/~elec539/Projects97/cult/node2.html, 2 pgs.
(Continued)

*Primary Examiner* — Xin Jia
(74) *Attorney, Agent, or Firm* — Merchant & Gould P.C.

(57) ABSTRACT

A method and system for creating a dynamic self-learning medical image network system, wherein the method includes receiving, from a first node initial user interaction data pertaining to one or more user interactions with the one or more initially obtained medical images; training a deep learning algorithm based at least in part on the initial user interaction data received from the node; and transmitting an instance of the trained deep learning algorithm to the first node and/or to one or more additional nodes, wherein at each respective node to which the instance of the trained deep
(Continued)

learning algorithm is transmitted, the trained deep learning algorithm is applied to respective one or more subsequently obtained medical images in order to obtain a result.

21 Claims, 13 Drawing Sheets

Related U.S. Application Data

(60) Provisional application No. 62/522,241, filed on Jun. 20, 2017.

(51) Int. Cl.
```
G06N 3/04      (2023.01)
G06N 3/08      (2023.01)
G06F 18/40     (2023.01)
G06F 18/214    (2023.01)
G06F 18/21     (2023.01)
G06V 10/774    (2022.01)
G06V 10/82     (2022.01)
```

(52) U.S. Cl.
CPC ............ *G06F 18/40* (2023.01); *G06N 3/04* (2013.01); *G06N 3/08* (2013.01); *G06V 10/774* (2022.01); *G06V 10/82* (2022.01); *G06V 2201/03* (2022.01)

(58) Field of Classification Search
CPC ....... A61B 6/467; A61B 6/468; A61B 5/0062; A61B 5/055; A61B 6/025; A61B 6/03; A61B 5/7267; A61B 5/7282; A61B 6/5217; G06F 18/214; G06F 18/217; G06F 18/40; G06N 3/04; G06N 3/08; G06N 3/082; G06N 3/045; G06N 3/063; G06V 10/774; G06V 10/82; G06V 2201/03; G16H 40/67; G16H 50/20; G16H 50/70; G16H 30/40

See application file for complete search history.

(56) References Cited

U.S. PATENT DOCUMENTS

| | | |
|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,641 A | 12/1985 | Caugant et al. |
| 4,706,269 A | 11/1987 | Reina et al. |
| 4,727,565 A | 2/1988 | Ericson |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 6/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,660,185 A | 8/1997 | Shmulewitz et al. |
| 5,668,889 A | 9/1997 | Hara |
| 5,671,288 A | 9/1997 | Wilhelm et al. |
| 5,712,890 A | 1/1998 | Spivey |
| 5,719,952 A | 2/1998 | Rooks |
| 5,735,264 A | 4/1998 | Siczek et al. |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,245,028 B1 | 6/2001 | Furst et al. |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |

(56) References Cited

U.S. PATENT DOCUMENTS

| | | |
|---|---|---|
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |
| 6,650,928 B1 | 11/2003 | Gailly |
| 6,683,934 B1 | 1/2004 | Zhao |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |
| 6,912,319 B1 | 5/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,554 B2 | 2/2006 | Mertelmeier |
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 | 5/2007 | Eberhard |
| 7,245,694 B2 | 7/2007 | Jing et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,634,050 B2 | 12/2009 | Muller et al. |
| 7,640,051 B2 | 12/2009 | Krishnan |
| 7,697,660 B2 | 4/2010 | Ning |
| 7,702,142 B2 | 4/2010 | Ren et al. |
| 7,705,830 B2 | 4/2010 | Westerman et al. |
| 7,760,924 B2 | 7/2010 | Ruth et al. |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | DeFreitas |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 * | 3/2017 | Gao .................. A61B 6/5211 |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,092,358 B2 | 10/2018 | DeFreitas |
| 10,111,631 B2 | 10/2018 | Gkanatsios |
| 10,242,490 B2 | 3/2019 | Karssemeijer |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2 | 3/2020 | Gkanatsios |
| 10,595,954 B2 | 3/2020 | DeFreitas |
| 10,624,598 B2 | 4/2020 | Chen |
| 10,977,863 B2 | 4/2021 | Chen |
| 10,978,026 B2 | 4/2021 | Kreeger |
| 11,419,565 B2 | 8/2022 | Gkanatsios |
| 11,508,340 B2 | 11/2022 | Kreeger |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1 | 5/2003 | Yanof |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0195433 A1 | 10/2003 | Turovskiy |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0064037 A1 | 4/2004 | Smith |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |

(56) References Cited

U.S. PATENT DOCUMENTS

| | | |
|---|---|---|
| 2004/0109529 A1 | 6/2004 | Eberhard et al. |
| 2004/0127789 A1 | 7/2004 | Ogawa |
| 2004/0138569 A1 | 7/2004 | Grunwald |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0047636 A1 | 3/2005 | Gines et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0084060 A1 | 4/2005 | Seppi et al. |
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2005/0135555 A1 | 6/2005 | Claus |
| 2005/0135664 A1 | 6/2005 | Kaufhold |
| 2005/0226375 A1 | 10/2005 | Eberhard |
| 2006/0009693 A1 | 1/2006 | Hanover et al. |
| 2006/0018526 A1 | 1/2006 | Avinash |
| 2006/0025680 A1 | 2/2006 | Jeune-Iomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0147099 A1 | 7/2006 | Marshall et al. |
| 2006/0155209 A1 | 7/2006 | Miller et al. |
| 2006/0197753 A1 | 9/2006 | Hotelling |
| 2006/0210131 A1 | 9/2006 | Wheeler |
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0274928 A1 | 12/2006 | Collins et al. |
| 2006/0291618 A1 | 12/2006 | Eberhard et al. |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios et al. |
| 2008/0043905 A1 | 2/2008 | Hassanpourgol |
| 2008/0045833 A1 | 2/2008 | DeFreitas et al. |
| 2008/0101537 A1 | 5/2008 | Sendai |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0221479 A1 | 9/2008 | Ritchie |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | DeFreitas |
| 2009/0005668 A1 | 1/2009 | West et al. |
| 2009/0005693 A1 | 1/2009 | Brauner |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0080752 A1 | 3/2009 | Ruth |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1 | 7/2009 | Ning |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1 | 2/2010 | Yu |
| 2010/0049046 A1 | 2/2010 | Peiffer |
| 2010/0054400 A1 | 3/2010 | Ren et al. |
| 2010/0079405 A1 | 4/2010 | Bernstein |
| 2010/0086188 A1 | 4/2010 | Ruth et al. |
| 2010/0088346 A1 | 4/2010 | Urness et al. |
| 2010/0098214 A1 | 4/2010 | Star-Lack et al. |
| 2010/0105879 A1 | 4/2010 | Katayose et al. |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0135558 A1 | 6/2010 | Ruth et al. |
| 2010/0152570 A1 | 6/2010 | Navab |
| 2010/0166267 A1 | 7/2010 | Zhang |
| 2010/0195882 A1 | 8/2010 | Ren et al. |
| 2010/0208037 A1 | 8/2010 | Sendai |
| 2010/0231522 A1 | 9/2010 | Li |
| 2010/0246909 A1 | 9/2010 | Blum |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |
| 2011/0087132 A1 | 4/2011 | DeFreitas et al. |
| 2011/0105879 A1 | 5/2011 | Masumoto |
| 2011/0109650 A1 | 5/2011 | Kreeger |
| 2011/0110576 A1 | 5/2011 | Kreeger |
| 2011/0125526 A1 | 5/2011 | Gustafson |
| 2011/0150447 A1 | 6/2011 | Li |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014504 A1 | 1/2012 | Jang |
| 2012/0014578 A1 | 1/2012 | Karssemeijer |
| 2012/0069951 A1 | 3/2012 | Toba |
| 2012/0106698 A1 | 5/2012 | Karim |
| 2012/0131488 A1 | 5/2012 | Karlsson et al. |
| 2012/0133600 A1 | 5/2012 | Marshall |
| 2012/0133601 A1 | 5/2012 | Marshall |
| 2012/0134464 A1 | 5/2012 | Hoernig et al. |
| 2012/0148151 A1 | 6/2012 | Hamada |
| 2012/0189092 A1 | 7/2012 | Jerebko |
| 2012/0194425 A1 | 8/2012 | Buelow |
| 2012/0238870 A1 | 9/2012 | Smith et al. |
| 2012/0293511 A1 | 11/2012 | Mertelmeier |
| 2013/0022165 A1 | 1/2013 | Jang |
| 2013/0044861 A1 | 2/2013 | Muller |
| 2013/0059758 A1 | 3/2013 | Haick |
| 2013/0108138 A1 | 5/2013 | Nakayama |

(56) References Cited

U.S. PATENT DOCUMENTS

| | | |
|---|---|---|
| 2013/0121569 A1 | 5/2013 | Yadav |
| 2013/0121618 A1 | 5/2013 | Yadav |
| 2013/0202168 A1 | 8/2013 | Jerebko |
| 2013/0259193 A1 | 10/2013 | Packard |
| 2014/0033126 A1 | 1/2014 | Kreeger |
| 2014/0035811 A1 | 2/2014 | Guehring |
| 2014/0064444 A1 | 3/2014 | Oh |
| 2014/0073913 A1 | 3/2014 | DeFreitas et al. |
| 2014/0219534 A1 | 8/2014 | Wiemker et al. |
| 2014/0219548 A1 | 8/2014 | Wels |
| 2014/0327702 A1 | 11/2014 | Kreeger et al. |
| 2014/0328517 A1 | 11/2014 | Gluncic |
| 2015/0052471 A1 | 2/2015 | Chen |
| 2015/0061582 A1 | 4/2015 | Smith |
| 2015/0238148 A1 | 8/2015 | Georgescu |
| 2015/0302146 A1 | 10/2015 | Marshall |
| 2015/0309712 A1 | 10/2015 | Marshall |
| 2015/0317538 A1 | 11/2015 | Ren et al. |
| 2015/0331995 A1 | 11/2015 | Zhao |
| 2016/0000399 A1 | 1/2016 | Halmann et al. |
| 2016/0022364 A1 | 1/2016 | DeFreitas et al. |
| 2016/0051215 A1* | 2/2016 | Chen ............ G16H 30/40 715/771 |
| 2016/0078645 A1 | 3/2016 | Abdurahman |
| 2016/0140749 A1 | 5/2016 | Erhard |
| 2016/0228034 A1 | 8/2016 | Gluncic |
| 2016/0235380 A1 | 8/2016 | Smith |
| 2016/0367210 A1 | 12/2016 | Gkanatsios |
| 2017/0071562 A1 | 3/2017 | Suzuki |
| 2017/0262737 A1* | 9/2017 | Rabinovich ............ G06F 18/24 |
| 2018/0047211 A1 | 2/2018 | Chen et al. |
| 2018/0137385 A1 | 5/2018 | Ren |
| 2018/0144244 A1* | 5/2018 | Masoud ............... G06N 3/105 |
| 2018/0256118 A1 | 9/2018 | DeFreitas |
| 2019/0015173 A1 | 1/2019 | DeFreitas |
| 2019/0043456 A1 | 2/2019 | Kreeger |
| 2019/0290221 A1 | 9/2019 | Smith |
| 2020/0046303 A1 | 2/2020 | DeFreitas |
| 2020/0093562 A1 | 3/2020 | DeFreitas |
| 2020/0184262 A1 | 6/2020 | Chui |
| 2020/0205928 A1 | 7/2020 | DeFreitas |
| 2020/0253573 A1 | 8/2020 | Gkanatsios |
| 2020/0345320 A1 | 11/2020 | Chen |
| 2020/0390404 A1 | 12/2020 | DeFreitas |
| 2021/0000553 A1 | 1/2021 | St. Pierre |
| 2021/0100518 A1 | 4/2021 | Chui |
| 2021/0100626 A1 | 4/2021 | St. Pierre |
| 2021/0113167 A1 | 4/2021 | Chui |
| 2021/0118199 A1 | 4/2021 | Chui |
| 2022/0005277 A1 | 1/2022 | Chen |
| 2022/0013089 A1 | 1/2022 | Kreeger |
| 2022/0192615 A1 | 6/2022 | Chui |
| 2022/0386969 A1 | 12/2022 | Smith |
| 2023/0053489 A1 | 2/2023 | Kreeger |
| 2023/0054121 A1 | 2/2023 | Chui |
| 2023/0056692 A1 | 2/2023 | Gkanatsios |
| 2023/0082494 A1 | 3/2023 | Chui |
| 2023/0125385 A1 | 4/2023 | Solis |
| 2023/0225821 A1 | 7/2023 | DeFreitas |

FOREIGN PATENT DOCUMENTS

| | | |
|---|---|---|
| CN | 202161328 | 3/2012 |
| CN | 102429678 | 5/2012 |
| CN | 107440730 | 12/2017 |
| DE | 102010009295 | 8/2011 |
| DE | 102011087127 | 5/2013 |
| EP | 775467 | 5/1997 |
| EP | 982001 | 3/2000 |
| EP | 1428473 | 6/2004 |
| EP | 2236085 | 6/2010 |
| EP | 2215600 | 8/2010 |
| EP | 2301432 | 3/2011 |
| EP | 2491863 | 8/2012 |
| EP | 1986548 | 1/2013 |
| EP | 2656789 | 10/2013 |
| EP | 2823464 | 1/2015 |
| EP | 2823765 | 1/2015 |
| EP | 3060132 | 4/2019 |
| JP | H09-198490 | 7/1997 |
| JP | H09-238934 | 9/1997 |
| JP | H10-33523 | 2/1998 |
| JP | 2000-200340 | 7/2000 |
| JP | 2002-109510 | 4/2002 |
| JP | 2002-282248 | 10/2002 |
| JP | 2003-189179 | 7/2003 |
| JP | 2003-199737 | 7/2003 |
| JP | 2003-531516 | 10/2003 |
| JP | 2004254742 | 9/2004 |
| JP | 2006-519634 | 8/2006 |
| JP | 2006-312026 | 11/2006 |
| JP | 2007-130487 | 5/2007 |
| JP | 2007-330334 | 12/2007 |
| JP | 2007-536968 | 12/2007 |
| JP | 2008-068032 | 3/2008 |
| JP | 2009-034503 | 2/2009 |
| JP | 2009-522005 | 6/2009 |
| JP | 2009-526618 | 7/2009 |
| JP | 2009-207545 | 9/2009 |
| JP | 2010-137004 | 6/2010 |
| JP | 2011-110175 A | 6/2011 |
| JP | 2012-011255 | 1/2012 |
| JP | 2012-501750 | 1/2012 |
| JP | 2012-061196 | 3/2012 |
| JP | 2013-244211 | 12/2013 |
| JP | 2014-507250 | 3/2014 |
| JP | 2014-534042 | 12/2014 |
| JP | 2015-506794 | 3/2015 |
| JP | 2015-144632 A | 8/2015 |
| JP | 2016-198197 | 12/2015 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 2005051197 | 6/2005 |
| WO | 2005/110230 | 11/2005 |
| WO | 2005110230 | 11/2005 |
| WO | 2005/112767 | 12/2005 |
| WO | 2005112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008047270 | 4/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | 2013/035026 | 3/2013 |
| WO | 2013/078476 | 5/2013 |
| WO | 2013/123091 | 8/2013 |
| WO | 2014/080215 | 5/2014 |
| WO | 2014/149554 | 9/2014 |
| WO | 2014/207080 | 12/2014 |
| WO | 2015/061582 | 4/2015 |
| WO | 2015/066650 | 5/2015 |
| WO | 2015/130916 | 9/2015 |

(56) References Cited

FOREIGN PATENT DOCUMENTS

| WO | 2016/103094 | 6/2016 |
|---|---|---|
| WO | 2016/184746 | 11/2016 |
| WO | 2018/183548 | 10/2018 |
| WO | 2018/183549 | 10/2018 |
| WO | 2018/183550 | 10/2018 |
| WO | 2018/236565 | 12/2018 |
| WO | 2021/021329 | 2/2021 |

OTHER PUBLICATIONS

"Supersonic to feature Aixplorer Ultimate at ECR", AuntiMinnie.com, 3 pages (Feb. 2018).

Al Sallab et al., "Self Learning Machines Using Deep Networks", Soft Computing and Pattern Recognition (SoCPaR), 2011 Int'l. Conference of IEEE, Oct. 14, 2011, pp. 21-26.

Berg, WA et al., "Combined screening with ultrasound and mammography vs mammography alone in women at elevated risk of breast cancer", JAMA 299:2151-2163, 2008.

Burbank, Fred, "Stereotactic Breast Biopsy: Its History, Its Present, and Its Future", published in 1996 at the Southeastern Surgical Congress, 24 pages.

Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.

Caroline, B.E. et al., "Computer aided detection of masses in digital breast tomosynthesis: A review", 2012 International Conference on Emerging Trends in Science, Engineering and Technology (Incoset), Tiruchirappalli, 2012, pp. 186-191.

Carton, AK, et al., "Dual-energy contrast-enhanced digital breast tomosynthesis—a feasibility study", BR J Radiol. Apr. 2010;83 (988):344-50.

Chan, Heang-Ping et al., "ROC Study of the effect of stereoscopic imaging on assessment of breast lesions," Medical Physics, vol. 32, No. 4, Apr. 2005, 1001-1009.

Chen, SC, et al., "Initial clinical experience with contrast-enhanced digital breast tomosynthesis", Acad Radio. Feb. 2007 14(2):229-38.

Diekmann, Felix., et al., "Digital mammography using iodine-based contrast media: initial clinical experience with dynamic contrast medium enhancement", Invest Radiol 2005; 40:397-404.

Dromain C., et al., "Contrast enhanced spectral mammography: a multi-reader study", RSNA 2010, 96th Scientific Assembly and Scientific Meeting.

Dromain, C., et al., "Contrast-enhanced digital mammography", Eur J Radiol. 2009; 69:34-42.

Dromain, Clarisse et al., "Dual-energy contrast-enhanced digital mammography: initial clinical results", European Radiology, Sep. 14, 2010, vol. 21, pp. 565-574.

E. Shaw de Paredes et al., "Interventional Breast Procedure", published Sep./Oct. 1998 in Curr Probl Diagn Radiol, pp. 138-184. (D15 in oppo).

eFilm Mobile HD by Merge Healthcare, web site: http://itunes.apple.com/bw/app/efilm-mobile-hd/id405261243?mt=8, accessed on Nov. 3, 2011 (2 pages).

eFilm Solutions, eFilm Workstation (tm) 3.4, website: http://estore.merge.com/na/estore/content.aspx?productID=405, accessed on Nov. 3, 2011 (2 pages).

Ertas, M. et al., "2D versus 3D total variation minimization in digital breast tomosynthesis", 2015 IEEE International Conference on Imaging Systems and Techniques (IST), Macau, 2015, pp. 1-4.

European Search Report in Application18820591.8, dated Mar. 4, 2021, 9 pages.

Fischer Imaging Corp, Mammotest Plus manual on minimally invasive breast biopsy system, 2002, 8 pages. (Reference labeled D13 in 01 Opposition).

Fischer Imaging Corporation, Installation Manual, MammoTest Family of Breast Biopsy Systems, 86683G, 86684G, P-55957-IM, Issue 1, Revision 3, Jul. 2005, 98 pages. (Reference labeled D12 in 01 Opposition).

Fischer Imaging Corporation, Operator Manual, MammoTest Family of Breast Biopsy Systems, 86683G, 86684G, P-55956-OM, Issue 1, Revision 6, Sep. 2005, 258 pages. (Reference labeled D11 in 01 Opposition).

Freiherr, G., "Breast tomosynthesis trials show promise", Diagnostic Imaging—San Francisco 2005, V27; N4:42-48.

Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages. (Reference labeled D10 in 0020 Opposition).

Ghiassi, M. et al., "A Dynamic Architecture for Artificial Networks", Neurocomputing, vol. 63, Aug. 20, 2004, pp. 397-413.

Giger et al. "Development of a smart workstation for use in mammography", in Proceedings of SPIE, vol. 1445 (1991), pp. 101103; 4 pages.

Giger et al., "An Intelligent Workstation for Computer-aided Diagnosis", in RadioGraphics, May 1993, 13:3 pp. 647-656; 10 pages.

Hologic, "Lorad StereoLoc II" Operator's Manual 9-500-0261, Rev. 005, 2004, 78 pgs.

Hologic, Inc., 510(k) Summary, prepared Nov. 28, 2010, for Affirm Breast Biopsy Guidance System Special 510(k) Premarket Notification, 5 pages.

Hologic, Inc., 510(k) Summary, prepared Aug. 14, 2012, for Affirm Breast Biopsy Guidance System Special 510(k) Premarket Notification, 5 pages.

ICRP Publication 60: 1990 Recommendations of the International Commission on Radiological Protection, 12 pages.

Jochelson, M., et al., "Bilateral Dual Energy contrast-enhanced digital mammography: Initial Experience", RSNA 2010, 96th Scientific Assembly and Scientific Meeting, 1 page.

Jong, RA, et al., Contrast-enhanced digital mammography: initial clinical experience. Radiology 2003; 228:842-850.

Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009. (Reference labeled D10 in 01 Opposition).

Kopans, et. al. Will tomosynthesis replace conventional mammography? Plenary Session SFN08: RSNA 2005.

Lehman, CD, et al. MRI evaluation of the contralateral breast in women with recently diagnosed breast cancer. N Engl J Med 2007; 356:1295-1303.

Lewin, JM, et al., Dual-energy contrast-enhanced digital subtraction mammography: feasibility. Radiology 2003; 229:261-268.

Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.

Lindfors, KK, et al., Dedicated breast CT: initial clinical experience. Radiology 2008; 246(3): 725-733.

Niklason, L., et al., Digital tomosynthesis in breast imaging. Radiology. Nov. 1997; 205(2):399-406.

Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).

PCT International Preliminary Report on Patentability in International Application PCT/US2018/035331, dated Jan. 2, 2020, 9 pages.

PCT International Search Report and Written Opinion in International Application PCT/US2018/035331, dated Sep. 7, 2018, 12 pages.

Pediconi, "Color-coded automated signal intensity-curve for detection and characterization of breast lesions: Preliminary evaluation of new software for MR-based breast imaging," International Congress Series 1281 (2005) 1081-1086.

Poplack, SP, et al., Digital breast tomosynthesis: initial experience in 98 women with abnormal digital screening mammography. AJR Am J Roentgenology Sep. 2007 189(3):616-23.

Prionas, ND, et al., Contrast-enhanced dedicated breast CT: initial clinical experience. Radiology. Sep. 2010 256(3):714-723.

Rafferty, E. et al., "Assessing Radiologist Performance Using Combined Full-Field Digital Mammography and Breast Tomosynthesis

(56) References Cited

OTHER PUBLICATIONS

Versus Full-Field Digital Mammography Alone: Results" . . . presented at 2007 Radiological Society of North America meeting, Chicago IL.
Reynolds, April, "Stereotactic Breast Biopsy: A Review", Radiologic Technology, vol. 80, No. 5, Jun. 1, 2009, pp. 447M-464M, XP055790574.
Sakic et al., "Mammogram synthesis using a 3D simulation. I. breast tissue model and image acquisition simulation" Medical Physics. 29, pp. 2131-2139 (2002).
Samani, A. et al., "Biomechanical 3-D Finite Element Modeling of the Human Breast Using MRI Data", 2001, IEEE Transactions on Medical Imaging, vol. 20, No. 4, pp. 271-279.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., "Full field breast tomosynthesis", Radiol Manage. Sep.-Oct. 2005; 27(5):25-31.
Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.
Van Schie, Guido, et al., "Mass detection in reconstructed digital breast tomosynthesis volumes with a computer-aided detection system trained on 2D mammograms", Med. Phys. 40(4), Apr. 2013, 41902-1-41902-11.
Weidner N, et al., "Tumor angiogenesis and metastasis: correlation in invasive breast carcinoma", New England Journal of Medicine 1991; 324:1-8.
Weidner, N, "The importance of tumor angiogenesis: the evidence continues to grow", Am J Clin Pathol. Nov. 2004 122(5):696-703.
Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your- hospital-pacs-on-your-ipad/, accessed on Nov. 3, 2011 (3 pages).
Yin, H.M., et al., "Image Parser: a tool for finite element generation from three-dimensional medical images", BioMedical Engineering Online. 3:31, pp. 1-9, Oct. 1, 2004.
Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.
Conner, Peter, "Breast Response to Menopausal Hormone Therapy—Aspects on Proliferation, apoptosis and Mammographic Density", 2007 Annals of Medicine, 39;1, 28-41.

Glick, Stephen J., "Breast CT", Annual Rev. Biomed. Eng., 2007, 9;501-26.
Metheany, Kathrine G. et al., "Characterizing anatomical variability in breast CT images", Oct. 2008, Med. Phys. 35 (10); 4685-4694.
Dromain, Clarisse, et al., "Evaluation of tumor angiogenesis of breast carcinoma using contrast-enhanced digital mammography", AJR: 187, Nov. 2006, 16 pages.
Zhao, Bo, et al., "Imaging performance of an amorphous selenium digital mammography detector in a breast tomosynthesis system", May 2008, Med. Phys 35(5); 1978-1987.
Mahesh, Mahadevappa, "AAPM/RSNA Physics Tutorial for Residents—Digital Mammography: An Overview", Nov.-Dec. 2004, vol. 24, No. 6, 1747-1760.
Zhang, Yiheng et al., "A comparative study of limited-angle cone-beam reconstruction methods for breast tomosynthesis", Med Phys., Oct. 2006, 33(10): 3781-3795.
Sechopoulos, et al., "Glandular radiation dose in tomosynthesis of the breast using tungsten targets", Journal of Applied Clinical Medical Physics, vol. 8, No. 4, Fall 2008, 161-171.
Wen, Junhai et al., "A study on truncated cone-beam sampling strategies for 3D mammography", 2004, IEEE, 3200-3204.
Ijaz, Umer Zeeshan, et al., "Mammography phantom studies using 3D electrical impedance tomography with numerical forward solver", Frontiers in the Convergence of Bioscience and Information Technologies 2007, 379-383.
Kao, Tzu-Jen et al., "Regional admittivity spectra with tomosynthesis images for breast cancer detection", Proc. of the 29th Annual Int'l. Conf. of the IEEE EMB, Aug. 23-26, 2007, 4142-4145.
Varjonen, Mari, "Three-Dimensional Digital Breast Tomosynthesis in the Early Diagnosis and Detection of Breast Cancer", IWDM 2006, LNCS 4046, 152-159.
Taghibakhsh, f. et al., "High dynamic range 2-TFT amplified pixel sensor architecture for digital mammography tomosynthesis", IET Circuits Devices Syst., 2007, 1(10, pp. 87-92.
Chan, Heang-Ping et al., "Computer-aided detection system for breast masses on digital tomosynthesis mammograms: Preliminary Experience", Radiology, Dec. 2005, 1075-1080.
Kopans, Daniel B., "Breast Imaging", 3rd Edition, Lippincott Williams and Wilkins, published Nov. 2, 2006, pp. 960-967.
Williams, Mark B. et al., "Optimization of exposure parameters in full field digital mammography", Medical Physics 35, 2414 (May 20, 2008); doi: 10.1118/1.2912177, pp. 2414-2423.
Elbakri, Idris A. et al., "Automatic exposure control for a slot scanning full field digital mammography system", Med. Phys. 2005; Sep; 32(9):2763-2770, Abstract only.
Feng, Steve Si Jia, et al., "Clinical digital breast tomosynthesis system: Dosimetric Characterization", Radiology, Apr. 2012, 263(1); pp. 35-42.

* cited by examiner

DYNAMIC SELF-LEARNING MEDICAL IMAGE METHOD AND SYSTEM

CROSS-REFERENCE TO RELATED APPLICATIONS

This application is a continuation of U.S. patent application Ser. No. 16/623,372, filed Dec. 16, 2019, now U.S. Pat. No. 11,403,483, which is a National Stage Application of PCT/US2018/035331, filed May 31, 2018, which claims priority to and the benefit of U.S. Patent Application Ser. No. 62/522,241, filed Jun. 20, 2017, the disclosures of which are incorporated herein by reference.

FIELD

The presently disclosed inventions relate generally to medical imaging techniques such as tomosynthesis, and more specifically to systems and methods for implementing a dynamic self-learning medical image network system. In particular, the presently disclosed inventions relate to interacting with, and observing user behavior pertaining to, one or more medical images at a plurality of nodes, in order to improve performance of the dynamic self-learning medical image network system.

BACKGROUND

Medical imaging systems, e.g., tomosynthesis systems, CT scanning systems, MRI systems, mammography systems, etc., have been used for screening and diagnosing a variety of conditions. Doctors and other medical professionals often rely on medical images to diagnose various health conditions. Accurate readings of the medical images are contingent on the quality and clarity of the image, as well as the knowledge and expertise of the medical professional reviewing the image. Specifically, in order for the medical images to be helpful to medical professionals, they must clearly and accurately portray respective body parts to which the image pertains, such that the medical professional can efficiently make a prognosis with reasonable certainty. Radiologists (or other medical professionals) typically study thousands of such medical images, and are trained to detect, through time and practice, recurring patterns in the medical images that are indicative of abnormalities (or other objects of interest) in human tissue.

However, even with extensive training, the objects of interest to the medical professional can be difficult to identify within the medical image for a number of reasons. For example, the medical image may not provide sufficient clarity, or focus, such that a potential abnormality is overlooked. Or, the abnormality may be too small, or otherwise difficult to ascertain. In another example, the abnormality may not be a well-known abnormality, or one that a newly-trained medical professional has previously encountered. In some cases, human error may result in certain abnormalities being overlooked or misdiagnosed. Furthermore, the experience and knowledge from highly experienced practitioners is not easily transferred to others. As will be appreciated, such errors and omissions may have serious, and sometimes even fatal, consequences for patients. Also, existing medical imaging analysis systems, including in particular Computer Aided Detection (CAD) systems, must be frequently programmed and modelled with new information and/or updated analysis techniques, which is time consuming and resource-intensive. Thus, a medical imaging analysis system that minimizes reviewing errors and is automatically updated to provide the latest information and analysis techniques would be highly desirable.

SUMMARY

In accordance with one aspect of the disclosed inventions, a method is provided for creating and using a dynamic self-learning medical image network system. In an exemplary embodiment, the method includes receiving, from a first node initial user interaction data pertaining to one or more user interactions with the one or more initially obtained medical images; training a deep learning algorithm based at least in part on the initial user interaction data received from the node; and transmitting an instance of the trained deep learning algorithm to the first node and/or to one or more additional nodes, wherein at each respective node to which the instance of the trained deep learning algorithm is transmitted, the trained deep learning algorithm is applied to respective one or more subsequently obtained medical images in order to obtain a result.

By way of non-limiting examples, the initial user interaction data may include at least one annotation on at least one of the one or more initially obtained medical images, a selection of one of more pixels associated with at least one of the one or more initially obtained medical images, an actual or estimated amount of time one or more users spent viewing one or more of the initially obtained medical images, an actual or estimated portion of at least one of the one or more medical images that was focused upon by at least one user, a description of a patient condition, and/or diagnostic findings that may be (without limitation) in a form of a written or a voice dictation report.

By way of non-limiting examples, the instance of the trained deep learning algorithm may be maintained at the first node and/or one or more additional nodes, and/or may run on a server accessed through a network.

By way of non-limiting examples, the result may include recognizing one or more objects in the medical image and/or providing a recommendation pertaining to the medical image.

In an exemplary embodiment, the method further includes receiving, from the first node and/or one or more additional nodes, subsequent user interaction data pertaining to one or more subsequently obtained medical images, wherein the subsequent user interaction data is used to modify the trained deep learning algorithm. By way of non-limiting example, the subsequent user interaction data may be used to modify the trained deep learning algorithm if it is determined that the subsequent user interaction data satisfies a predetermined threshold confidence level indicating that the trained deep learning algorithm should be modified. By way of non-limiting example, modification of the trained deep learning algorithm may include adding one or more layers to and/or changing the internal structure of, the layers in the trained deep learning algorithm.

In accordance with another aspect of the disclosed inventions, a dynamic self-learning medical image network system is provided, the system including a plurality of nodes, and a central brain server, wherein the central brain server is configured to receive initial user interaction data from one or more nodes of the plurality, wherein the initial user interaction data pertains to one or more user interactions with one or more initially obtained medical images, train a deep learning algorithm based at least in part on the initial user interaction data received from the node, and transmit an instance of the trained deep learning algorithm to each node of the plurality, and wherein each node of the plurality is configured to apply the instance of the trained deep learning algorithm to one or more subsequently obtained medical images in order to obtain a result.

In an exemplary embodiment, each node of the plurality is configured to maintain an instance of the trained deep learning algorithm.

By way of non-limiting examples, the initial user interaction data received by the central brain server may include at least one annotation on at least one of the one or more initially obtained medical images, a selection of one of more pixels associated with at least one of the one or more initially obtained medical images, an actual or estimated amount of time one or more users spent viewing one or more of the initially obtained medical images, an actual or estimated portion of at least one of the one or more medical images that was focused upon by at least one user at one of the nodes, a description of a patient condition, and/or diagnostic findings that may be (without limitation) in a form of a written or a voice dictation report.

By way of non-limiting examples, the result may include recognizing one or more objects in the medical image and/or providing a recommendation pertaining to the medical image.

In an exemplary embodiment, the central brain server is configured to receive subsequent user interaction data from one or more nodes of the plurality pertaining to one or more subsequently obtained medical images, and to modify the trained deep learning algorithm if the subsequent user interaction data satisfies a predetermined threshold confidence level indicating that the trained deep learning algorithm should be modified. By way of non-limiting example, central brain server may modify the trained deep learning algorithm by adding one or more layers to the trained deep learning algorithm.

These and other aspects and embodiments of the disclosed inventions are described in more detail below, in conjunction with the accompanying figures.

BRIEF DESCRIPTION OF THE FIGURES

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION OF THE ILLUSTRATED EMBODIMENTS

Figure 1:
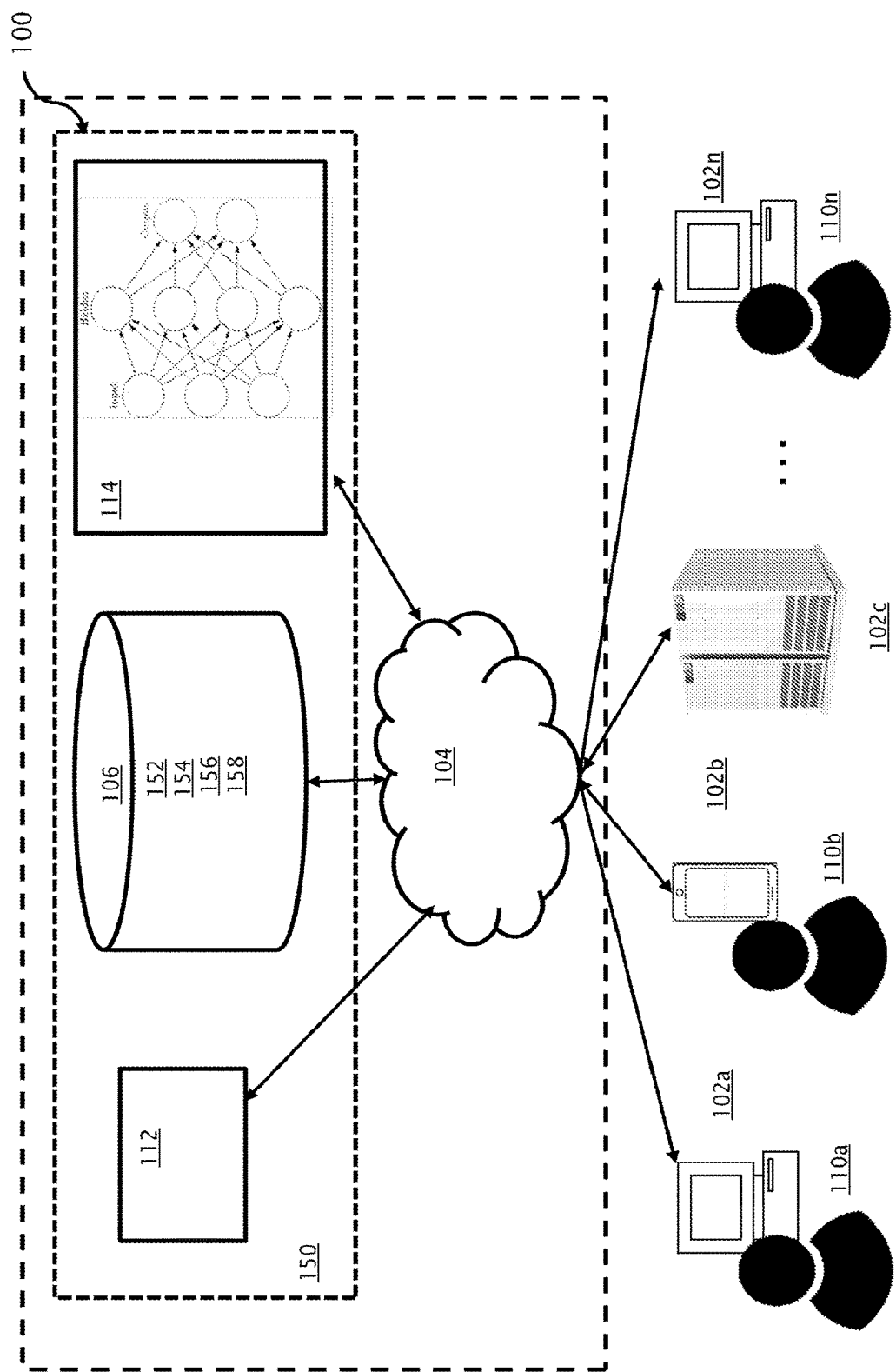
FIG. 1 is a block diagram illustrating the dynamic self-learning medical image network system constructed in accordance with embodiments of the disclosed inventions.

All numeric values are herein assumed to be modified by the terms "about" or "approximately," whether or not explicitly indicated, wherein the terms "about" and "approximately" generally refer to a range of numbers that one of skill in the art would consider equivalent to the recited value (i.e., having the same function or result). In some instances, the terms "about" and "approximately" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. In describing the depicted embodiments of the disclosed inventions illustrated in the accompanying figures, specific terminology is employed in this patent specification for the sake of clarity and ease of description. However, the disclosure of this specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this specification, including without limitation the accompanying figures and the appended claims.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the disclosed inventions, which is defined only by the appended claims and their equivalents. In addition, an illustrated embodiment of the disclosed inventions needs not have all the aspects or advantages shown. For example, an aspect or an advantage described in conjunction with a particular embodiment of the disclosed inventions is not necessarily limited to that embodiment and can be practiced in any other embodiments even if not so illustrated.

Introduction

This patent specification and the accompanying figures describe and illustrate a dynamic self-learning medical image network system that utilizes deep learning techniques to observe user interactions with medical images at a plurality of nodes. These user interactions are compiled, analyzed and optimized using a central brain network that advantageously trains one or more deep learning algorithms/network to continuously improve readings of medical images over time. As will be discussed throughout the specification, the dynamic self-learning medical image network system advantageously leverages expertise gained from users who are highly trained in reading medical images and decodes this information in deep learning algorithms, such that the system is constantly learning and improving analysis of medical images over time, in an effort to ultimate emulate the skill and intuition of a human expert.

Accurate reading of medical images, such as without limitation MRI scans, CT scans, tomosynthesis slices, X-rays, etc., is often contingent on the skill and technical expertise of medical personnel evaluating them. This expertise is gained through time, practice and intuition that is developed as a result of viewing a very large number of medical images. However, since there is a wide range in the respective skill, efficiency and expertise of the medical personnel charged with reading the images, the quality and accuracy of image-based screening and diagnosis can vary greatly. Further, even in the case of highly skilled medical professionals (e.g., radiologists), human error sometimes causes missed diagnoses, inaccurate readings and/or false positives. Of course, such errors, although easy to make, adversely affect the quality of healthcare delivered to patients, and can cause great stress and anxiety to everyone involved.

Although there are many medical image analysis software (CAD) programs available in the market today, they are static modelling programs that have to be programmed and trained prior to implementation, and as such can quickly become outdated. Re-programming to update the system is costly and time intensive, and still tends to lag behind research or new findings, even if routinely performed.

Advantages of the Dynamic Self-Learning Medical Image Network

One approach to globally improve the quality of medical image screening and diagnosis is to aid the reader of the medical images (also referred to herein as the system "user") by implementing a dynamic self-learning medical imaging network system that interacts with a large number of users (e.g., expert radiologists), analyzes many types of medical data, e.g., medical images, patient information data, patient medical records, etc., and automatically learns to interpret medical images and data to identify patterns (which may be image patterns or non-image patterns) that are symptomatic of abnormalities.

A dynamic self-learning medical image network system may be defined as a system that is continuously updating and/or adding layers to one or more deep neural networks, without necessarily requiring manual re-programming. In other words, rather than relying (and waiting) on presumed (if not actual) experts that understand trends in radiology or image analysis to create a new static program or update an existing one, the dynamic self-learning system is continually learning from the actual (and truly expert) users, by analyzing the user interactions with the system and periodically adding layers to the deep neural networks based on this analysis. This approach has several advantages. First, by studying user interactions with a very large number of medical images, the accuracy of the system in detecting such patterns not only improves over time, but also contemporaneously with the user. For example, if users are beginning to identify a previously unknown mass as being an abnormality, the dynamic self-learning medical image network system obtains this information in real-time, and is able to start identifying such abnormalities on its own, without necessarily being re-programmed by a system administrator. Additionally, the system learns patterns not just from a limited training dataset, but from a very large, and indeed ever-growing dataset. For example, thousands of radiologists may mark a particular type of breast mass as a spiculated mass (e.g., a type of breast cancer lesion). Having digital data of these diagnoses allows the system to study the patterns of the images that have been marked by the users as constituting a spiculated mass. Thus, the dynamic self-learning system described and depicted herein may strategically leverage the expertise of tens (or hundreds) of thousands of users in real-time to develop a highly accurate image recognition system.

Further, the dynamic self-learning medical image network system described and depicted herein allows users to rely on the system (and other users) in reaching a diagnosis. For example, a particular doctor (or group of doctors) may have special expertise when dealing with a rare form of abnormality. Or the abnormality may have only been recently detected by a small group of users in a particular part of the world. By leveraging knowledge that may only be available in one local community, the dynamic self-learning system may assist users in other communities worldwide by automatically detecting the heretofore unknown or little-known condition. Thus, information may spread far more swiftly with such an integrated image recognition system that is connected to users having varying skills, expertise, geography and patient type.

Moreover, by tracking interactions of a large number of users, the dynamic self-learning system may learn that certain users are especially skilled or knowledgeable, e.g., based on the rate of accurate screenings, and interactions with such users may be weighted higher than the average user of the medical image system. Conversely, if it is determined that certain users are less skilled, the dynamic self-learning system may avoid or minimize learnings from such user interactions, but may instead assist such users with information gained from users that have greater expertise. Thus, the dynamic self-learning medical image network system may actively assist users in improving readings of medical images.

The dynamic self-learning medical image network system may be trained to observe a set of user interactions pertaining to one or more medical images, and pool data received from a plurality of users in order to learn aspects pertaining to medical image and user interface interaction. For example, one learning aspect may relate to image analysis itself, and the dynamic self-learning medical image network system may observe user behavior related to medical image to detect recurring patterns in medical images that are indicative of abnormalities. Another example of a learning aspect may relate to user experience, and how to improve a set of task flows such that a user is provided an optimal amount of information to quickly and efficiently reach a prognosis. Yet another example of a learning aspect may relate to learning medical history associated with a patient and presenting that information to the medical professional to provide a more comprehensive diagnosis.

Although the present specification focusses on learning aspects related to image analysis and diagnosis, it should be appreciated and understood that the dynamic self-learning medical image network system may observe a myriad of user interactions to improve various aspects of the system. By constantly learning through user interactions with medical images in many locations, the dynamic self-learning medical image network system detects (or aids medical professionals in detecting) abnormalities, thereby increasing the efficiency and accuracy of screening and diagnoses performed using medical images. Ultimately, by learning details pertaining to highly skilled user decisions regarding medical images (also referred to herein as "medical image process flow"), the dynamic self-learning medical image network system becomes increasingly accurate and reliable over time, such that it may attempt to emulate the skill (or indeed even the subconscious intuition) of such highly skilled users.

The present specification focuses on implementing a dynamic self-learning medical image network system using deep machine learning algorithms (e.g., neural networks) to learn from users and data. It is envisioned that the system may learn independently with little need for manual programming or programmer input. In particular, in recent years, there have been major improvements in the field of machine learning using deep learning systems to recognize images and to understand natural languages. In many applications, the machine learning algorithm can be trained to learn to perform tasks at similar performance levels as a human. By building upon such machine learning algorithms, an "expert-level" self-learning medical image network system may be created that can be used to extract patterns and detect trends that may be too complex to be detected through traditional computer technologies but easily detected by an expert human user. Thus, the dynamic self-learning medical image network system may become an "expert" assistant to the medical professional reading the medical image. Other suitable means to achieve such a complex learning may be similarly implemented without limitation.

System Overview (Including Interaction Between Various Nodes and the Central Brain)

FIG. 1 illustrates an overview of the dynamic self-learning medical image network system 100 which incorporates image generation, image analysis and network technology. It should be understood that while FIG. 1 illustrates a particular embodiment with certain processes taking place in a particular serial order or in parallel, the claims and various other embodiments described herein are not limited to any particular order, unless so specified. More particularly, the dynamic self-learning medical image network system 100 includes a plurality of nodes 102 (e.g., 102a, 102b, 102c . . . 102n) that interact with a central brain network 104. In one or more embodiments, the nodes 102 refer to a computing system that may or may not interact with a user. As shown in FIG. 1, nodes 102a and 102b interact with the users, but node 102c does not. In some embodiments, the nodes 102 may refer to a point of contact between the dynamic self-learning medical image network system 100 and a user 110 (e.g., 110a, 110b . . . 110n). The nodes 102 may be any type of computing device including a processor and/or display system (e.g., personal computer, specialized imaging system, smartphone, a tablet, an image acquisition device, e.g., MRI, CT, tomosynthesis system), an image review workstation, a virtual reality device, desktop computer, web portal, etc. In some embodiments, the respective nodes may each be some other type of machine-human user interface.

Each node 102 may be implemented on a picture archiving and communications system (PACS). For example, a respective node 102 may be a dedicated medical image viewing workstation allowing users 110 to perform a variety of specialized image-related tasks. The nodes 102 may include one or more network interfaces for communicating with other devices through a network. The nodes 102 may include other input/output devices that enable user interaction with the node, such as a display, keyboard, mouse, audio speakers, and the like. It should be appreciated that the node may function with or without the user. For example, in some embodiments, the node 102 may be an intelligent workstation that mimics or attempts to make decisions like a human.

In some embodiments, a particular node 102 may represent an algorithm or data server that may be running data mining algorithms. In other embodiments, the node 102 may be a computing device that gathers data. In some embodiments, the node 102 may be a PACS machine that gathers images. In still other embodiments, the node 102 may simply be software that is running on a hospital computer system. Thus, it should be appreciated that not all nodes 102 necessarily interact with users, and some nodes 102 may simply gather data, or learn from data itself while other nodes 102 also provide and receive user interaction.

A user 110 accessing the dynamic self-learning medical image network system 100 is typically a medical professional (e.g., general doctor, radiologist, medical technician), but it should be appreciated that the dynamic self-learning medical image network system 100 is capable of interacting with any user (e.g., non-medical professionals, patients, etc.) no user at all. For purposes of illustration, the remainder of this specification focusses on medical professional users, but this should not be understood as limiting the applicability of the dynamic self-learning medical image network system.

The central brain network 104 may be any type of network known in the art, such as the Internet, or any cloud computing network. In one or more embodiments, the nodes 102 may communicatively couple to the central brain network in any manner, such as by a global or local wired or wireless connection (e.g., LAN, WAN, intranet, etc.). In one or more embodiments, the central brain network 104 may be communicatively coupled to one or more servers 150 or other machines which may include one or more processing units and/or computer readable media. In one or more embodiments, the central brain network 104 may reside (and be maintained) on one or more physical computing devices, or it may reside on a virtual cloud computing network. In its simplest form, it can be a very powerful central computing device communicatively coupled to a plurality of nodes. In a more complex form, the central brain network 104 may take a distributed form and reside over a number of physical or virtual computing devices.

More particularly, the server(s) 150 may house and/or host a plurality of computing components that together process data received from the plurality of nodes 102, store data, and provide outputs that are sent back to the nodes 102. As will be discussed in further detail below, the data may pertain to medical images being viewed and interacted with at the plurality of nodes 102. This data may be processed, analyzed, stored and updated through the various computing components of the server 150, and updated data may be sent back to the nodes 102 through the central brain network 104. In one or more embodiments, the server 150 may be a single powerful server. In another embodiment, a distributed system having multiple servers performing sub-sections of the computing tasks is envisioned. The server(s) 150 may be located in one geographical location, or may be located at different locations throughout the world. In one or more embodiments, an instance of the server 150 is operable to run at the node 102, such that an instance of the dynamic self-learning medical image network system runs on the node itself. The server(s) 150 may refer to local servers or remote servers.

In one or more embodiments, the server(s) 150 include one or more database(s) 106 that store all or portion of the data related to the dynamic self-learning medical image network system 100. The database(s) 106 may be the central data store providing long-term storage for all data, or it may be a limited-purpose data store for a specific area. The database(s) 106 make data accessible to the central brain network 104. The server(s) 150 may include computing components that are operable to retrieve data from the one or more databases and supply it to the central brain network 104 through a server-network interface. Although depicted as a single database 106 in FIG. 1, it should be appreciated that any number of local or remote databases may be part of the dynamic self-learning medical image network system 100. In one or more embodiments, the database 106 may store image acquisition data 154 that may be displayed to the users 110 at the various nodes 102. The database 106 may also store image analysis data 156, or data related to analysis of the various medical images. In one or more embodiments, training data 158 may also be used to train the dynamic self-learning medical image network system 100.

Medical images typically refer to digital representations of one or more objects (e.g., parts or portions of a patient's body, such as breasts). The digital representations may be modified or manipulated in order to identify or enhance certain features of the image. Such manipulations are virtual manipulations accomplished through the various computing components of the server(s) 150.

The analysis data may originate from the users or may be computer-generated analysis data. The database 106 may also store a set of user interaction data 152. The user interaction data 152 may be any data collected from the plurality of users 110. For example, the user interaction data 152 may be detected patterns indicative of known abnormalities, and also may contain feature values (e.g., coordinates, grayscale values, contrast values, etc.) related to abnormalities (e.g., cysts, tumors, abnormal masses, spiculated masses, calcifications, etc.). In one or more embodiments, the database(s) 106 include a constantly updated/modified learning library that improves over time based on the collected user interaction data. In one or more embodiments, the learning library may store a set of rules and/or models that may be used by the server(s) for image analysis.

In one or more embodiments, the server(s) 150 include one or more algorithms 112 that ingest a set of data pertaining to user interaction with a plurality of images, and create data models that may be used to detect patterns indicative of abnormalities in the medical images. The algorithms 112 may relate to image analysis, image display, or any other processes related to data that is present and interacted with at the nodes 102. Although the present specification focusses on image analysis algorithms, it should be appreciated that any type of algorithm 112 may be created and stored.

In one or more embodiments, the server(s) 150 include one or more deep learning algorithms or deep neural networks 114 that are trained on medical image data to learn complex image patterns and detect anatomical landmarks. A deep learning algorithm may refer to a deep neural network comprising various layers of information. Deep learning algorithms 114 contain multiple layers of learned features and/or variables between the input data and the output data. Deep learning algorithms 114 or deep neural networks may be implemented with many layers that are built on top of each other, such that complex deep learning algorithms comprise several deep layers, e.g., tens, hundreds, or even thousands of layers, that are continuously added as the system learns more information. A deep neural network may be differentiated with typical neural networks that tend to be "shallow" neural networks comprising only a few layers, e.g., only three or four layers. Thus, deep neural networks tend to be far more complex than shallow neural networks.

The deep learning algorithms 114 may be trained to detect patterns or a localization (e.g., pixel or voxel coordinates) in a medical image. In one or more embodiments, deep learning algorithms may be trained based on a plurality of training images. For example, the deep learning algorithms 114 may be trained using the user interaction data stored in the database(s) 106. The training images may be 2D or 3D medical images acquired through any type of medical image modality (e.g., tomosynthesis, mammography, CT, MRI, ultrasound, etc.). It should be appreciated that at least a subset of the training images may be annotated with the location of the respective anatomical object or landmark. For example, the user interaction data stored in the database(s) 106 may contain annotations (collected from the plurality of users 110) in the medical images identifying a desired object (e.g., type of mass, abnormality, type of tissue, etc.).

In some embodiments, the training images may be non-annotated but may tag objects in some other fashion. The deep learning algorithms 114 adapt and modify over time so as to improve their accuracy, efficiency and/or other performance criteria with a larger and larger number of user interaction data, thereby detecting and localizing desired anatomical landmarks or objects in the medical images with greater precision. Although there may be many possible implementations of deep learning algorithms to recognize abnormalities in medical images, one possible implementation approach includes one or more deep learning algorithms that calculate a probability that a targeted anatomical object is located at a particular pixel or voxel. In another possible implementation, the deep learning algorithms may calculate a difference vector from a particular voxel to a predicted location of the target object.

Thus, deep learning algorithms 114 may be utilized in one of many possible implementations and be trained, using user interaction data, to detect target objects or abnormalities in the medical images. By collecting vast amounts of user interaction data, the deep learning algorithms may be trained to become increasingly precise over time. It should be appreciated that that the deep neural networks or deep learning algorithms are updated dynamically, in contrast to static neural networks that are used to provide results based on a pre-programmed algorithm. Static neural networks do not adapt to new information, whereas the deep neural network system described and depicted herein "learns" from various user interactions, and updates, modifies and/or adds layers to the deep learning neural network(s). The term "dynamic," in this context, refers to a deep-learning system that is continually updated or modified automatically without specific need for re-programming. In particular, the deep neural network system preferably automatically updates the respective deep neural networks by adding one or more layers and/or changing the structure of one or more existing layers, once it is understood by the system that additional complexity pertaining to a pattern is required or otherwise useful. This is an important distinction from existing deep neural network algorithms, which (once trained) merely modify the respective layer weighting parameters without otherwise changing or adding layers.

There may be many ways in which to add layers to the deep neural network and/or update the deep neural network contemporaneously while a plurality of users interacts with the system. For example, the system might pool together data from a large number of users to determine a threshold level of confidence before adding a layer of complexity to the existing deep learning algorithm. The threshold levels may be predetermined, in one or more embodiment. Or, in another embodiment, the threshold level may refer to a particular number of users corroborating a particular detail. In yet another embodiment, programmer input may be requested prior to adding another layer. Once a particular confidence level is achieved, one or more layers may be added, or the neural network may be modified to conform to the newly "learned" data.

Example Implementation of Dynamic Self-Learning Medical Image Network System

Figure 2:
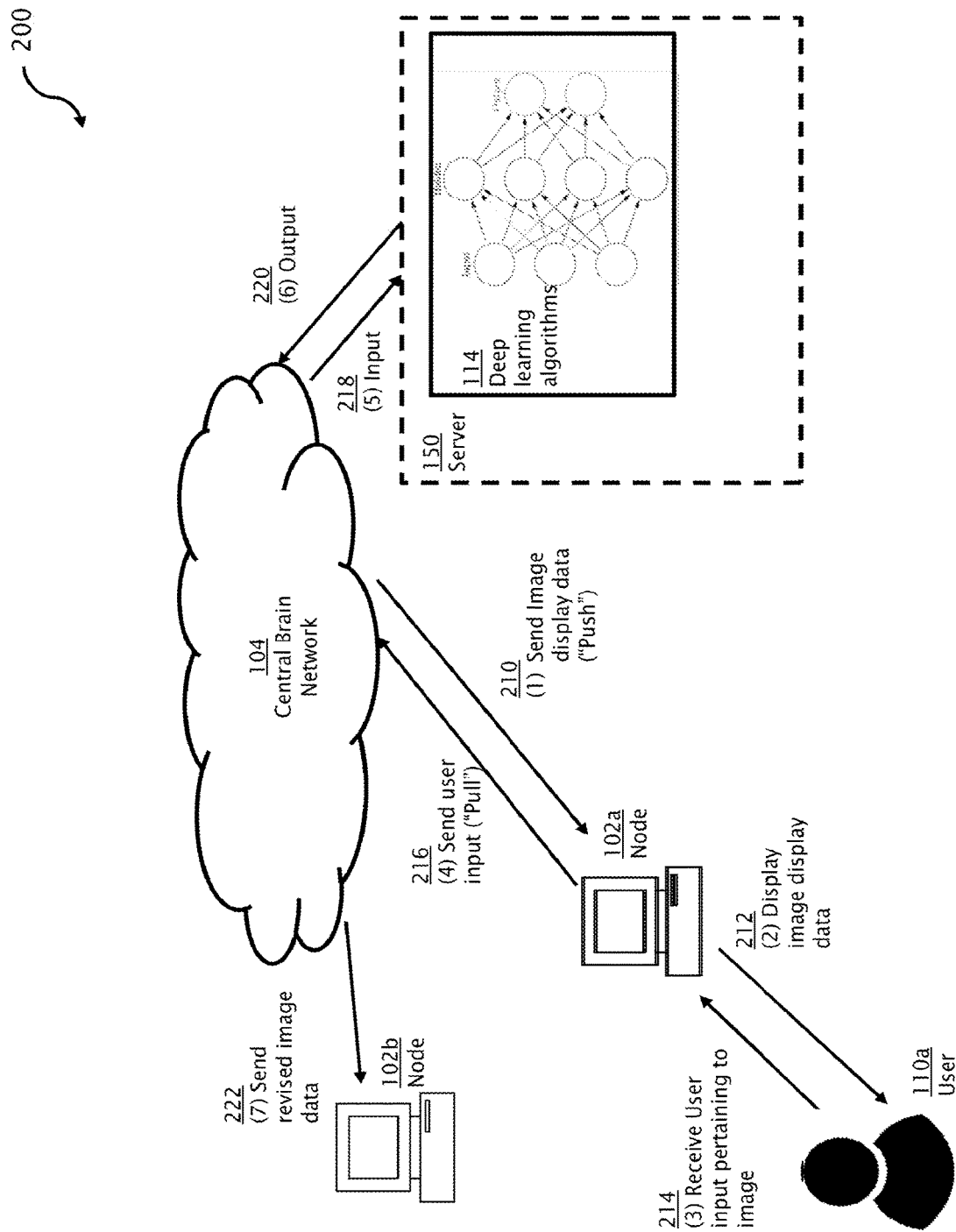
FIG. 2 is a sequence diagram illustrating the flow of information between a user and a central brain network constructed in accordance with embodiments of the disclosed inventions.

Referring now to FIG. 2, a system diagram showing an example sequence of interaction with the various components of the dynamic self-learning medical image network system is illustrated. As discussed in detail with reference to FIG. 1, at 210, a set of image display data may be sent to the node 102a through the central brain network 104. In one or more embodiments, an instance of an initial deep learning algorithm/network may also be sent to the node to perform image analysis. The initial deep learning algorithm may be trained at the central brain network using existing data, and known images, or training data. An instance of the initial deep learning algorithm may be pushed to one or more nodes of the dynamic self-learning image network system. In one or more embodiments, the image display data may be medical images (e.g., tomosynthesis image slices of a patient's breast tissue). At 212, the user 110a (if the node interacts with a user) interacts with the node 102a, and is able to view the image display data. In one or more embodiments, the initial deep learning algorithm may be run on the medical images, and one or more results may be provided to the user 110a.

At 214, the user may interact with the medical image (e.g., annotate the medical image, zoom into particular aspects of the medical image, focus on a particular slice if there are multiple slices, etc.) in one or more ways. For example, in viewing a particular tomosynthesis slice, the user may mark a particular set of pixels of the image and annotate that part of the image as indicative of a spiculated mass lesion. This user interaction may be recorded at the node 102a. The various types of possible user interactions will be discussed further below. Or, the user 110a may concur or reject the analysis provided by the deep learning algorithm. User interactions are collected in addition to the provided analysis such that the dynamic self-learning image network system is constantly collecting user interaction information even if a current instance of the (initially trained) deep-learning algorithm is run on one or more medical images.

At 216, the user interaction data recorded at the node 102a (e.g., annotations, marked pixels, audio and/or video recordings, etc.) may be sent to the central brain network 104. At 218, the user interaction data (input) is received at the server 15 through the central brain network 104. In one or more embodiments, the user interaction data may be used as additional training data on the deep learning algorithms 114. As discussed above, the deep learning algorithms 114 may consume the user interaction data to learn patterns or features associated with a spiculated mass as highlighted by the user. This interaction (along with other user interaction data collected from all the other nodes of the dynamic self-learning medical image network system) allows the deep learning algorithms 114 to automatically recognize spiculated masses (and other abnormalities learned by the deep learning algorithms 114) based on digital information associated with the medical image. The modified (improved) deep learning algorithm information may be stored at one or more databases at the server 150.

In practice, not every new user interaction data will be used (or be useful) to modify (with the goal of improving) an existing deep learning algorithm. The example discussed above is simplified for illustrative purposes. Rather, the newly collected user interaction data may be used to run one or more data-mining/un-supervised learning algorithm to form a new understanding of the complexity of the new data. Once this complexity reaches a certain threshold level, more layers may be added to the deep learning algorithm to create an improved/updated deep learning algorithm that is more complex and contains insights from more data. The improved/updated deep learning algorithm may be further trained on more preliminary/training data before it is pushed back to various nodes of the dynamic self-learning medical image network system.

At 220, the improved/updated deep learning algorithms are communicated to the various nodes through the central brain network 104. At 222, an instance (or partial instance) of the improved/updated trained deep learning algorithms may be transmitted to any node (e.g., 102b), which may then be used to provide feedback and/or provide image analysis at the node 102b. The improved/updated trained deep learning algorithms may run on the node 102b in order to automatically recognize spiculated masses (or other abnormalities) found in other medical images residing at the node 102b. For example, this improved/updated deep learning algorithm information may be used on another medical image viewed by a user at node 102b. The node 102b (leveraging the improved deep learning algorithms) may automatically mark portions of the other medical image if the system determines that a particular area of the medical image contains a spiculated mass object. This information may be displayed to the user at node 102b, wherein the user may confirm or reject the automatically detected object. This interaction may also be recorded and sent back to the server 150 through the central brain network 104 to further improve the deep learning algorithms 114. Thus, it is envisioned that the deep learning algorithms becomes increasingly skilled at recognizing objects found in the medical images over time.

As discussed above, user interaction data collected at the various nodes 102 of the dynamic self-learning medical image network system 100 is continuously used, in regular intervals, to improve the deep learning algorithms 114. Thus, the current invention(s) describe a dynamic self-learning medical image network system that is constantly learning in real-time as it is being deployed at various nodes. In contrast to static neural networks that have to be manually programmed or re-programmed periodically, the dynamic self-learning medical image network system is continuously adding more layers (or otherwise modifying itself) to the deep learning algorithms without necessitating reprogramming to create a new neural network. When new data is learned that adds to the complexity of the existing deep learning algorithms, new layers are automatically added to the deep learning algorithm, and pushed to the various nodes.

Figure 3:
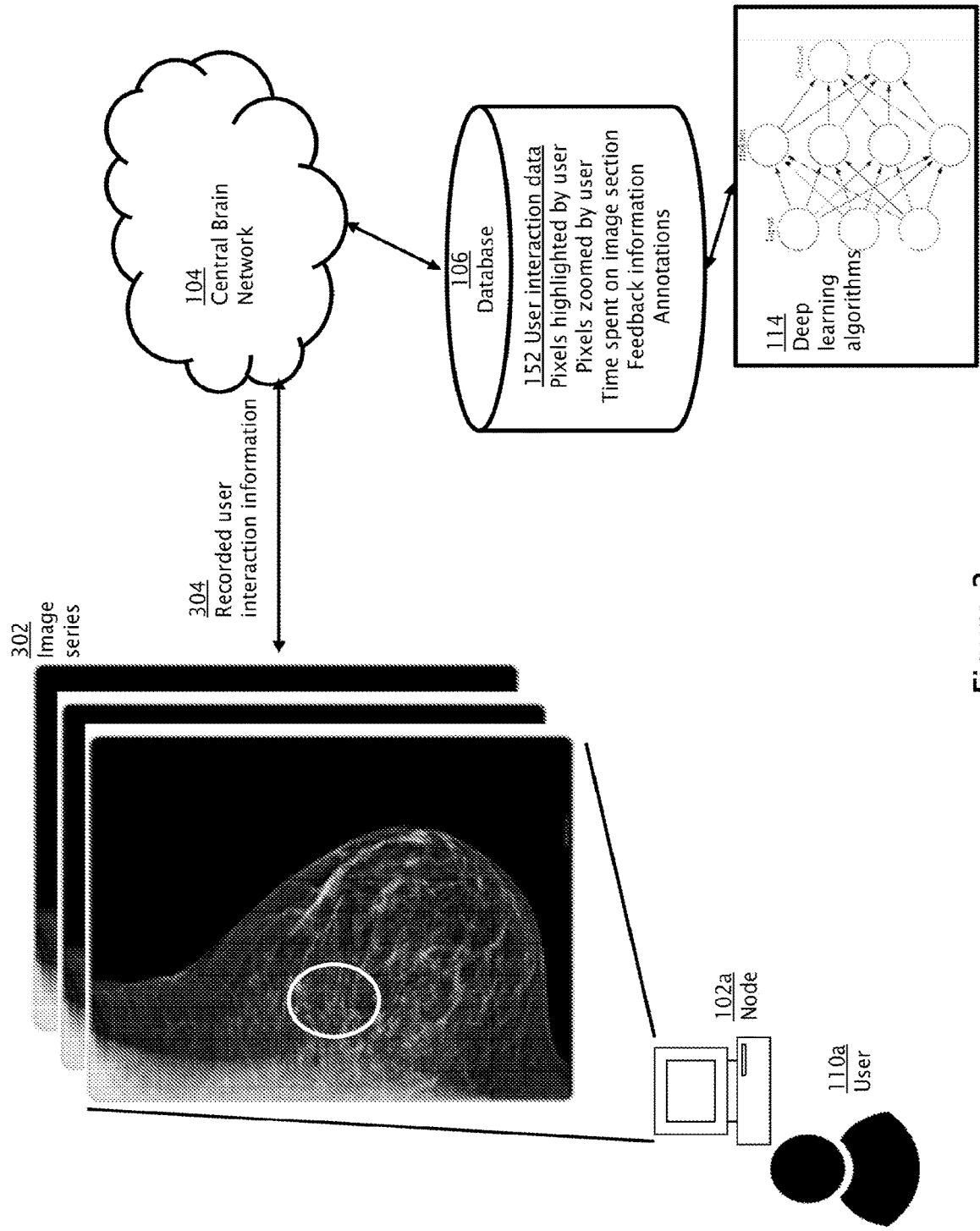
FIG. 3 illustrates one embodiment of recording user interactions in a dynamic self-learning medical image network system constructed in accordance with embodiments of the disclosed inventions.

Referring now to FIG. 3, an overview of how various types of user interactions with medical images is utilized in the dynamic self-learning medical image network system is illustrated. As shown in FIG. 3, the user 110a at the node 102a may be presented with a series of medical images 302. For example, the series of medical images 302 may be tomosynthesis slices representative of a patient's breast tissue. The user 110a may interact with the series of images 302 in a number of ways. For example, the user 110a may zoom in to view particular tomosynthesis slices. Also, the user 110a may concentrate on just a subset of the image slices, while ignoring the rest. Additionally, the user 110a may expressly mark a portion of the digital image, and annotate it. Furthermore, the user 110a may create a video or audio recording of the user's diagnosis.

In one or more embodiments, the user 110*a* may immediately focus one or more of the image slices 302 to focus on. For example, the user 110*a* may spend most of the time focused on image slice x. The dynamic self-learning medical image network system 100 may record this interaction to determine whether there are any patterns in what image slice(s) provide the most valuable information. In one or more embodiments, the dynamic self-learning medical image network system 100 may track the actual time and/or an estimate of an amount of time spent on a particular image or images (slice or slices). This information may be coupled with other collected user interaction data to learn what parts of an image deck are most important when analyzing images.

In another example, the dynamic self-learning medical image network system may ask the user 110*a* to mark or otherwise annotate a particular image with information regarding the medical image. In one possible implementation, a set of users may be selected to train the dynamic self-learning system. These users may be asked to annotate various medical images with many types of abnormalities. The system may thereafter pool images belonging to or associated with a type of abnormality, and then identify ("learn") patterns emerging from a relatively large image dataset.

Other types of user interactions that may be recorded include pixels of the medical image that may be highlighted or zoomed by the user. The dynamic self-learning medical image network system may record the time spent on an image or set of images. Similarly, any number of such interactions may be received and recorded.

Any or all of these user interactions 304 may be sent to the server 150 through the central brain network 104, and further stored in the learning database 106. The learning database 106 may comprise user interaction data 152 received from thousands or millions of nodes. As shown in FIG. 3, the user interaction data 152 may comprise pixels highlighted by the user, areas (e.g., defined by pixels) of an image that were focused upon (e.g., "zoomed in" on) by the user, actual or estimated time spent on image portions, feedback on images, annotations, or any other type of user interaction. Similarly, other types of user interactions (e.g., 154, 156 and 158) may be similarly stored, although omitted for simplicity in FIG. 3.

Furthermore, the learning database 106 may store information related to known digital patterns indicative of objects in the image. For example, the learning database 106 may store patterns indicative of various abnormal (and normal) objects found in the breast. The database 106 may also store a set of basic training data (e.g., known abnormalities, etc.) to be used to train the deep learning algorithms. Of course, by utilizing more and more training data, the deep learning algorithms become more accurate over time. By pooling together medical image data (image or non-image based data) deep learning algorithms and other types of machine learning algorithms may be utilized to learn data patterns that can be used to not only detect and localize abnormalities, but also to understand normal variations among different individuals and populations.

Figure 4A:
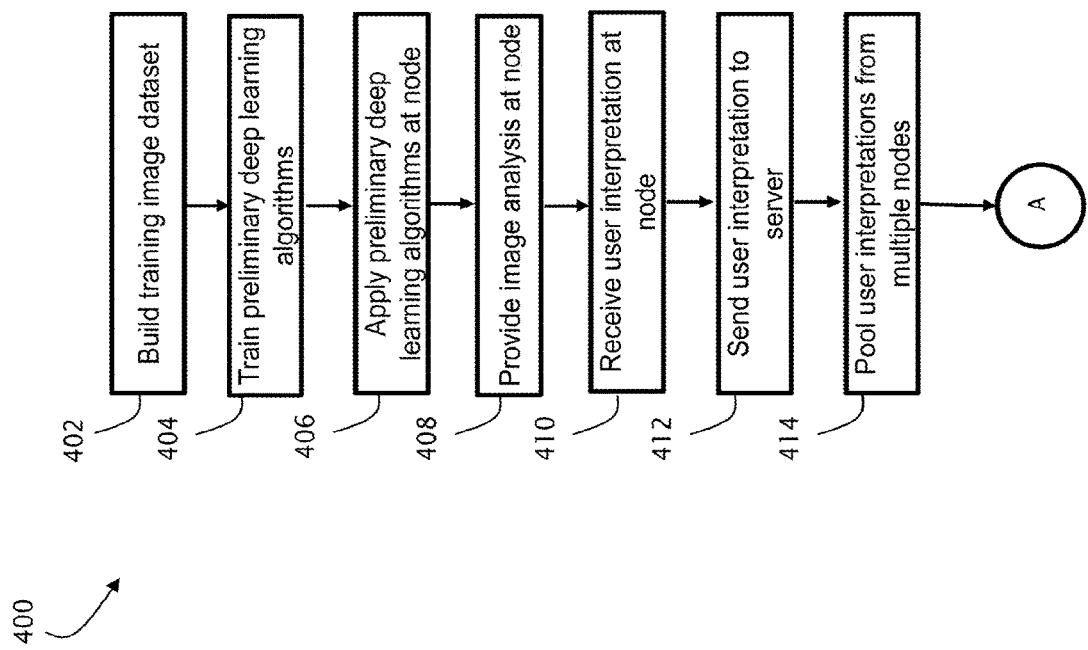
FIGS. 4A and 4B illustrate an exemplary flow diagram depicting various steps to modify (and thereby improve) the dynamic self-learning medical image network system over time.
Figure 4B:
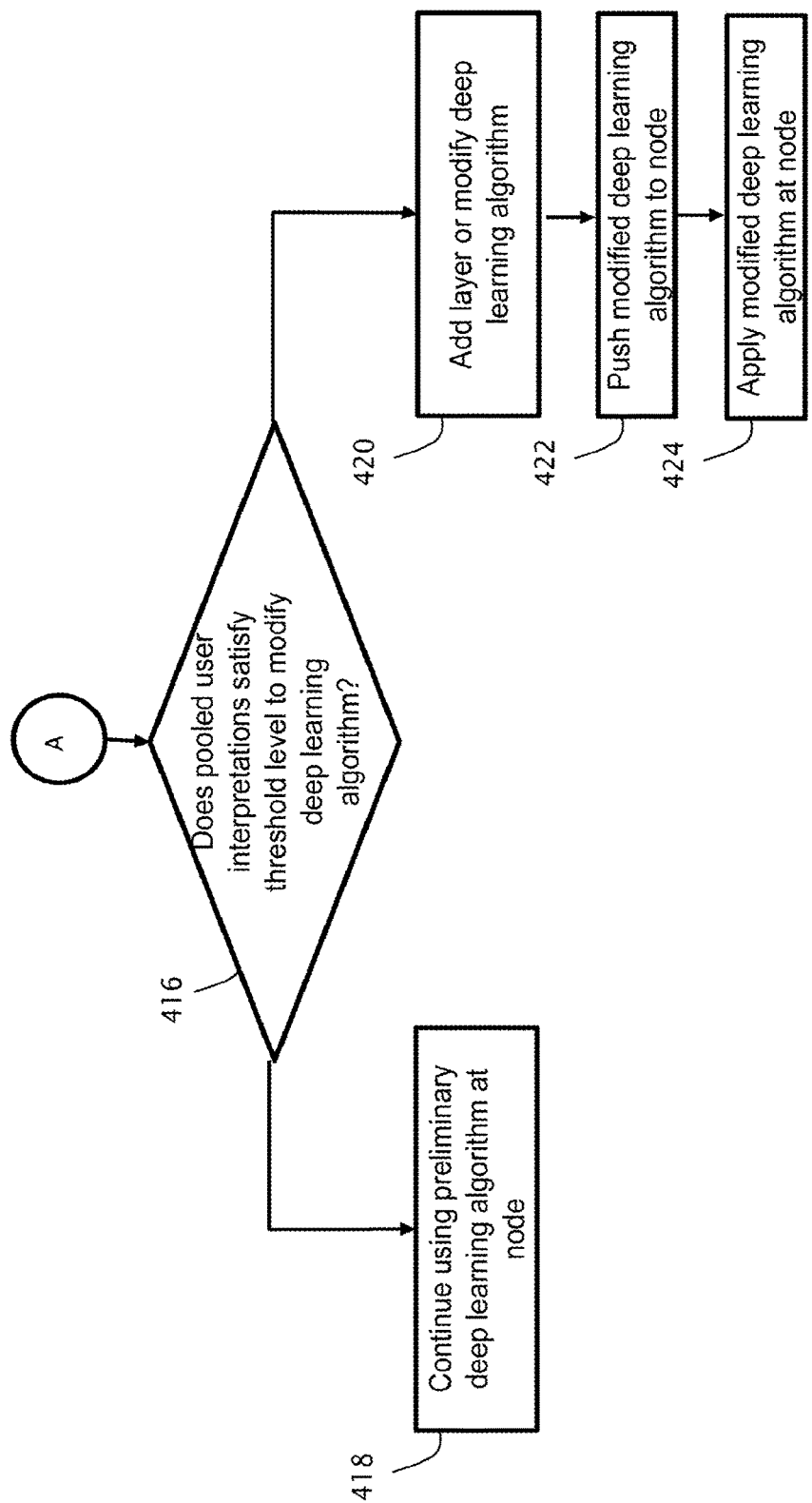

FIGS. 4A and 4B illustrate a flow diagram 400 provided to illustrate an exemplary process that may be performed in order to implement the dynamic self-learning medical image network system. At step 402, a training image dataset may be collected. For example, this initial image dataset may include a set of annotated medical images collected from a set of user experts. At step 404, this image dataset may be used to train a preliminary deep learning algorithm. At step 406, when a user 110*a* is viewing a new medical image, this preliminary deep learning algorithm may be applied. At step 408, an image analysis (indicating any detected abnormalities) may be provided at the node 102*a*. At step 410, user interaction data is received. For example, the user 110*a* may agree with the image analysis provided by the dynamic self-learning medical image network system, and indicate as much.

At step 412, the user interaction data may be sent from the node 102*a* to the server 150 through the central brain network 104. At step 414, the new user interaction data may be pooled with other user interpretation data related to a particular part of the deep learning algorithm. For example, the user interaction may pertain to a particular type of object being displayed at various nodes to various users. For example, a particular feature of an abnormal object may be specified through the user interaction. Each of these user interactions regarding the feature may be compiled together to determine whether users are identifying a particular feature, or else classifying it in a manner that is not presently encoded in the existing deep neural network or algorithm.

At step 416 it may be determined whether the pooled user interpretations satisfy a threshold level such that a modification to the preliminary deep learning algorithm is required. For example, the deep learning algorithm may only be modified, e.g., add a layer to the deep neural network, change a value, etc., if a predetermined threshold level is met. For example, to add a layer to the deep neural network, a confidence level, e.g., based on number of users providing the particular input, weight given to users, etc., of 98% may need to be met. Or, in another example, to change an existing value, a confidence level of 99.9% may need to be met.

At step 418, if the predetermined threshold level is not met, the system continues to use the preliminary deep learning algorithm. If, however, it is determined at step 416 that the threshold level is met, the deep learning algorithm may be modified (e.g., a new layer may be added). At step 422, the modified deep learning algorithm may be pushed to various nodes, and the modified deep learning algorithm may be applied to various images at the nodes (step 424).

It should be appreciated that in some embodiments, when the neural network is modified, it may need to be trained at the server with training data prior to pushing the algorithm to the various nodes. Thus, the above example is provided for illustrative purposes and should not be read as limiting.

Referring now to FIGS. 5A-5H an exemplary process flow diagram illustrating various steps in implementing the dynamic self-learning medical image network system is shown. It should be appreciated that the following scenario focuses on user-based interactions at the nodes, but other embodiments may entail simply collecting data from the node without any user interaction at all. Thus, again, the following described process is provided for purposes of illustration, and should not be read as limiting.

Figure 5A:
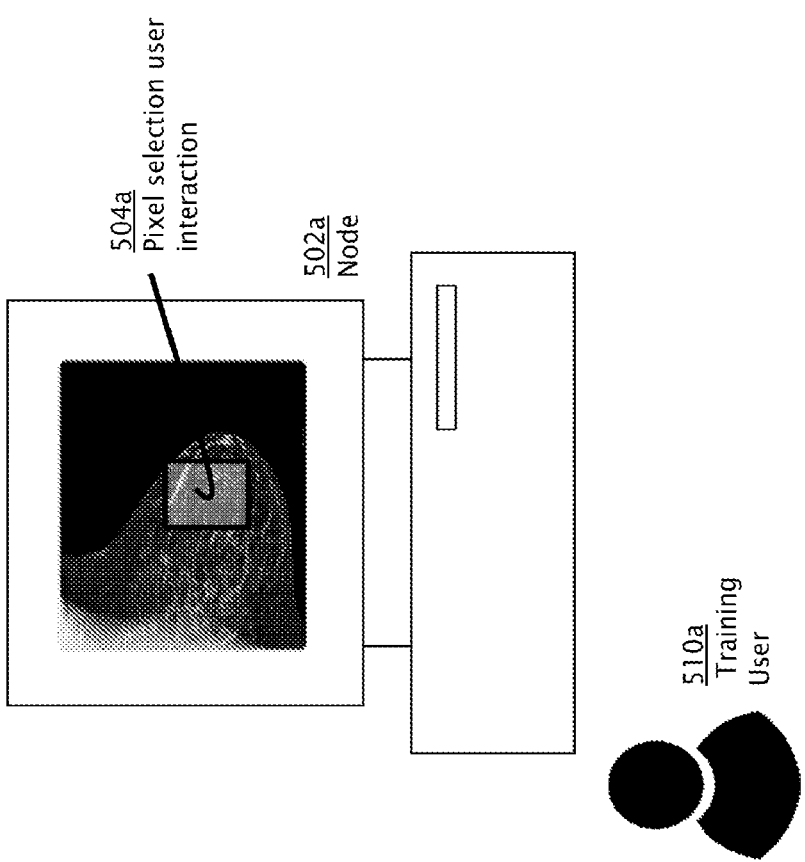
FIGS. 5A to 5H illustrate an exemplary process flow in accordance with embodiments of the disclosed inventions.

Referring to FIG. 5A, a training user 510*a* may interact with one or more medical image slices at a node 502*a*. In one or more embodiments, the training user may be a user that is chosen to train the dynamic self-learning medical image network system. In order embodiments, the training user may be a volunteer. In yet another embodiment, there may be no distinction between training users and regular users, and all user interactions with the dynamic self-learning medical image network system may be given the same weight. As shown in FIG. 5A, the training user 510*a* may interact with the medical image by selecting a group of pixels (504*a*). For example, the selected group of pixels may represent an area of the medical image containing one or more abnormalities (or other objects of interest).

Figure 5B:
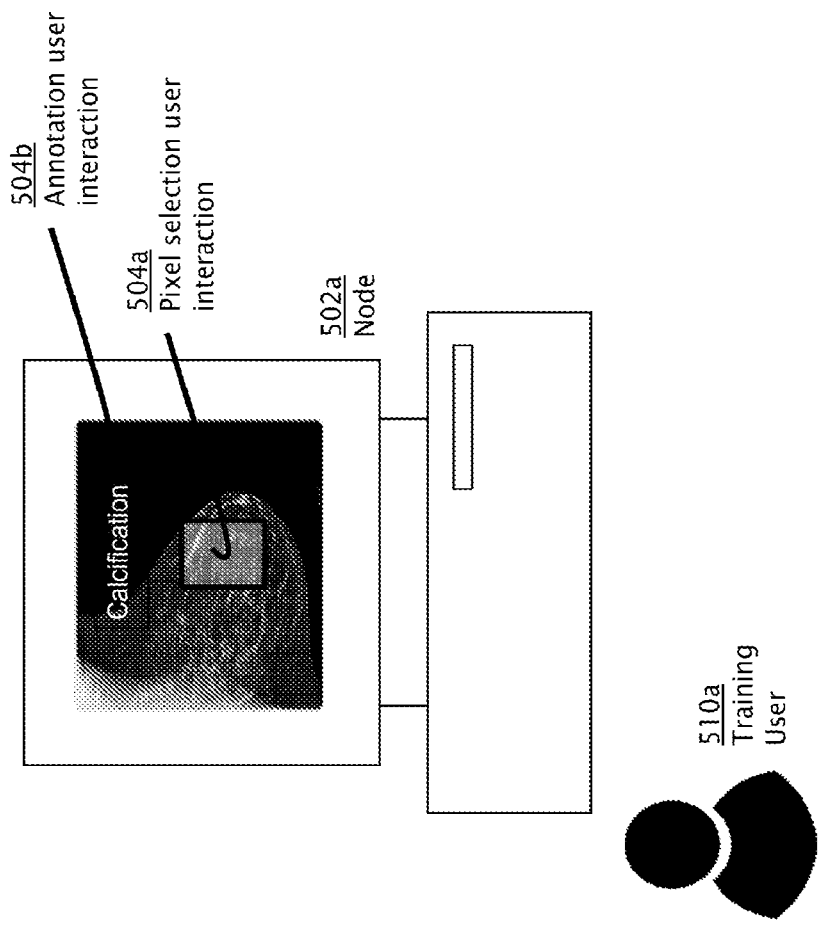
Figure 5C:
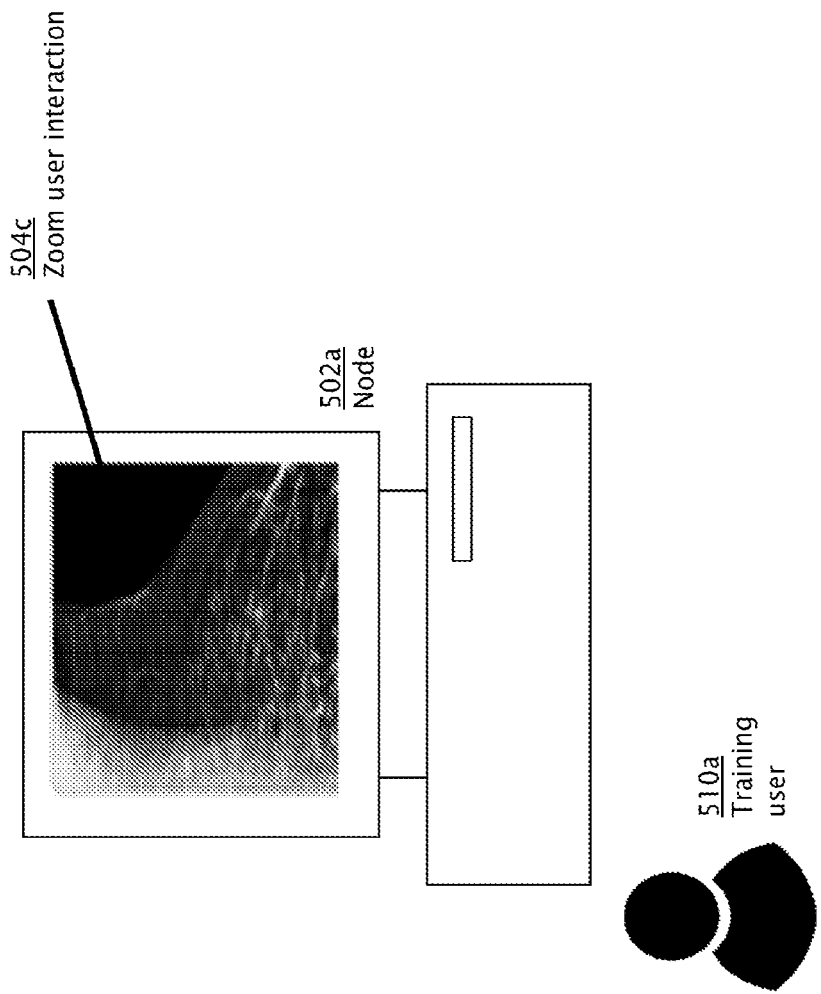

Referring now to FIG. 5B, the training user 510a may further annotate the one or more medical images (504b). In the illustrated embodiment, the user 510a may annotate the selected portion of the medical image to indicate that it pertains to a calcification object. FIG. 5C illustrates yet another user interaction 504c, where the system notes that the training user 510a zooms in on a particular area of the medical image.

Figure 5D:
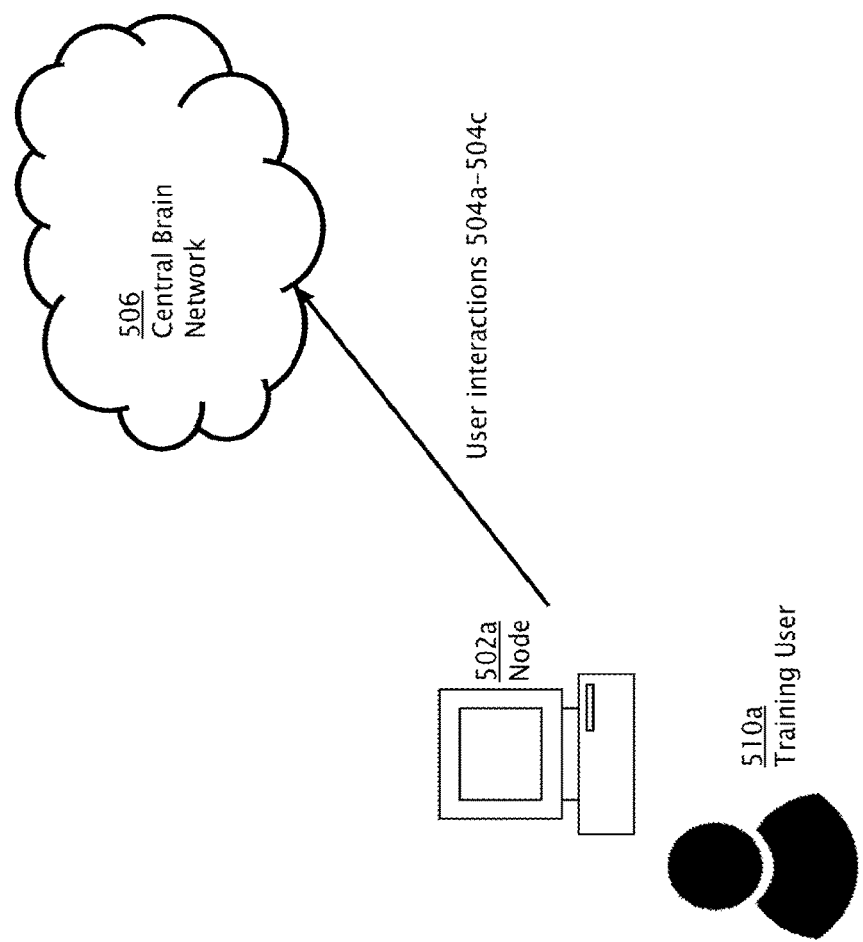

As shown in FIG. 5D, the user interactions 504a-504c are transmitted to the server 150 through the central brain network 506. It should be appreciated that in some embodiments, an instance of the dynamic self-learning medical image network system may reside at the node 502a itself. In other embodiments, the dynamic self-learning medical image network system may only be accessed through the central brain network 506.

Figure 5E:
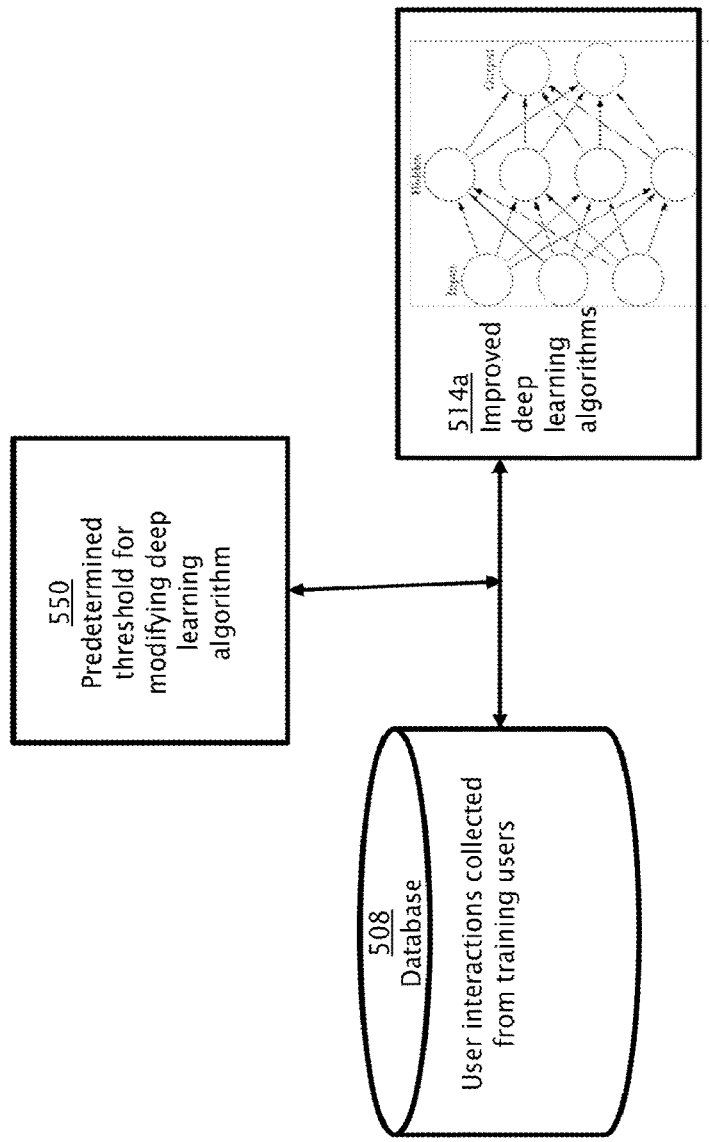

As shown in FIG. 5E, the user interactions 504a-504c may be stored in the database 508 associated with the dynamic self-learning medical image network system. This set of user interactions may be used to train the deep learning algorithms to result in a set of improved deep learning algorithms 514a. In the illustrated embodiment, the system consults with a predetermined threshold for modifying the deep learning algorithm 550 in order to determine whether the user input (e.g., pooled from various users) meets or exceeds the threshold. If the threshold is satisfied, the deep learning algorithm 514a is created. As discussed above, the improved deep learning algorithm 514a may be additional layers, modified values, or any other changes. It should be appreciated that this modification occurs without a need for re-programming of the neural network, and maybe done automatically by the dynamic self-learning medical image network system periodically whenever the threshold is met, in one or more embodiments.

Figure 5F:
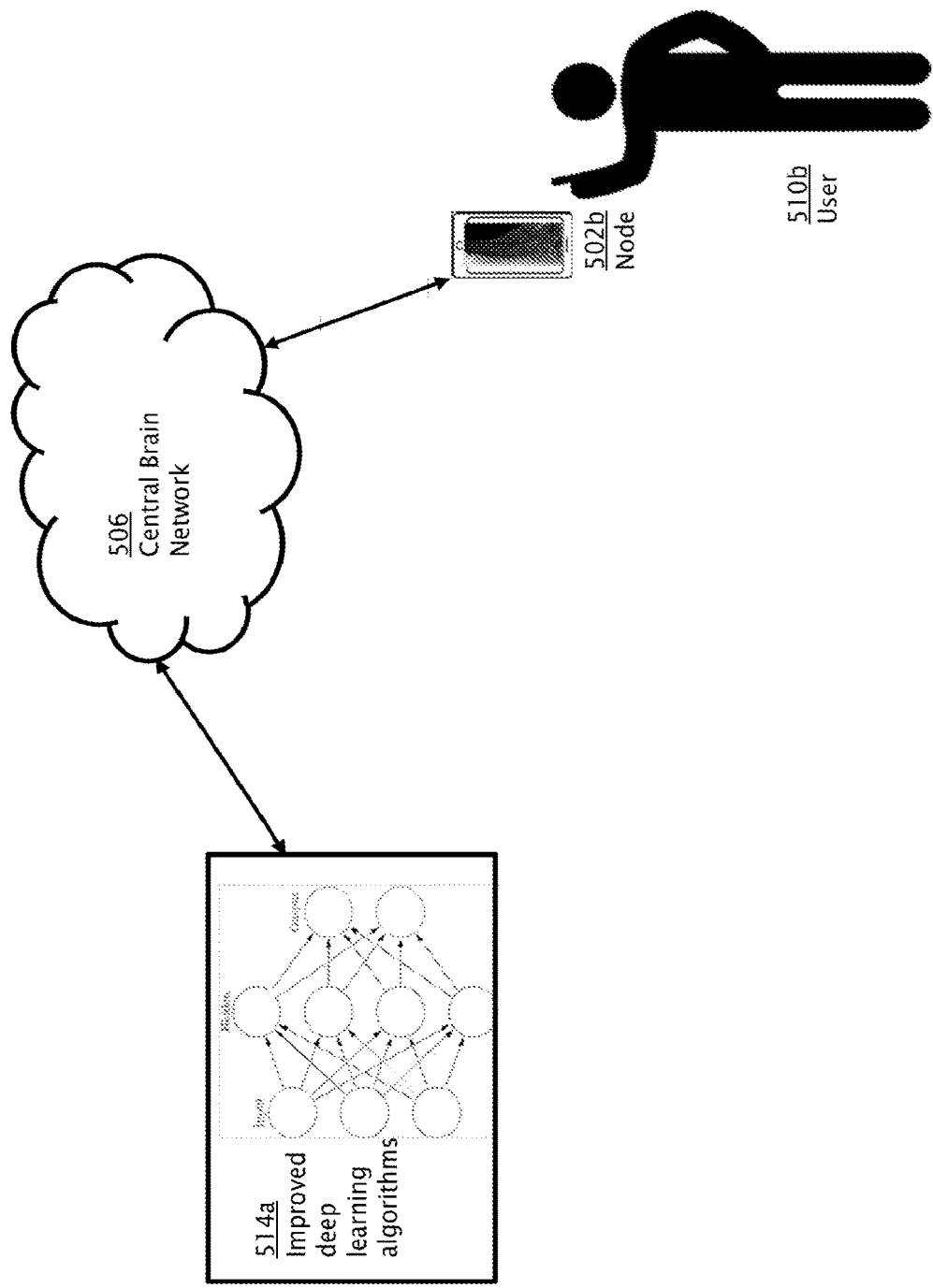
Figure 5G:
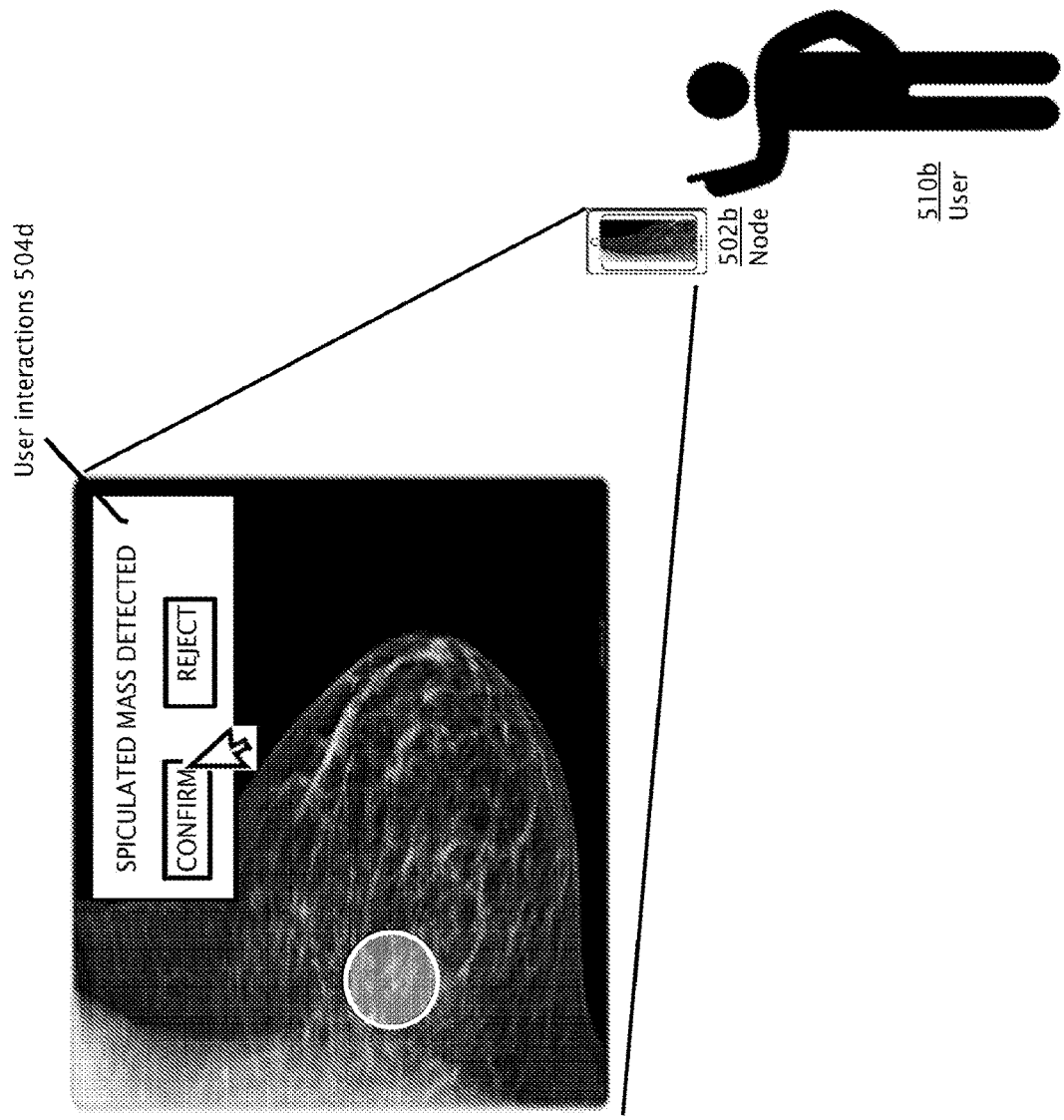

Referring now to FIG. 5F, the improved deep learning algorithm may be utilized at another node 502b, being accessed by another user 510b. In the illustrated embodiment, the other user 510b may be viewing a different set of medical images. As shown in FIG. 5G, the dynamic self-learning medical image network system may utilize the improved deep learning algorithm 514a to recognize one or more objects in the medical images being shown at node 502b. For example, a spiculated mass object may be detected, and the system may ask the user 510b to confirm or reject a recognized object. This user interaction 504d (e.g., confirm/reject) may be captured by the dynamic self-learning medical image network system.

Figure 5H:
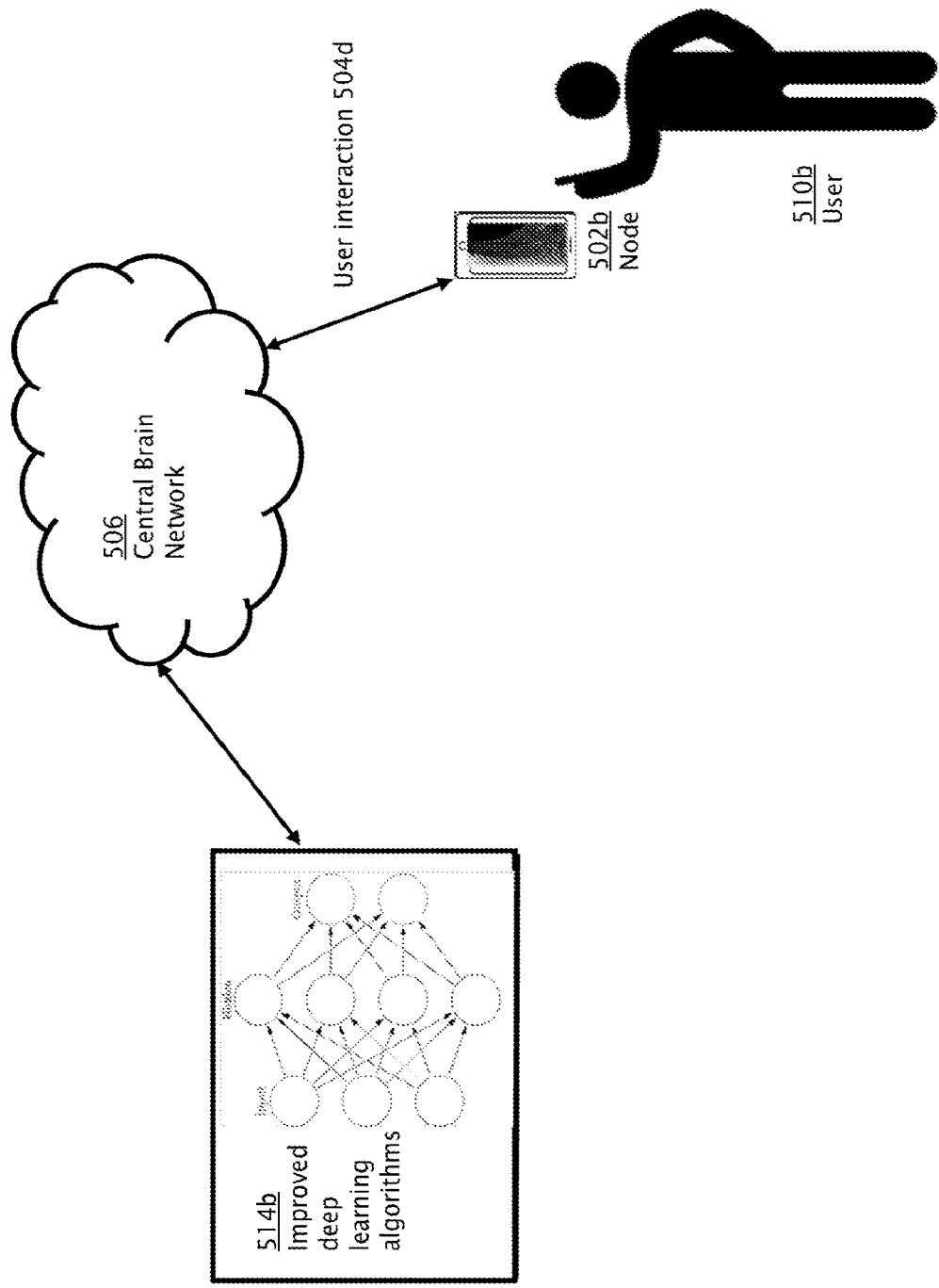

Finally, referring to FIG. 5H, user interaction 504d is used to improve the deep learning algorithms even further, thereby generating improved deep learning algorithms 514b. These improved deep learning algorithms 514b may be successfully used at other nodes to perform various analysis tasks. Thus, the dynamic self-learning medical image network system is greatly improved over time by receiving user interactions from a large number of users.

Having described exemplary embodiments of the dynamic self-learning medical image network system, it should be appreciated that the examples provided herein and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed inventions. It will also be apparent to those skilled in the art that various changes and modifications may be made to the depicted and/or described embodiments, without departing from the scope of the disclosed inventions, which is to be defined only by the following claims and their equivalents. The specification and drawings are, accordingly, to be regarded in an illustrative rather than restrictive sense.

What is claimed is:

1. A method for creating and using a dynamic self-learning medical image network system, the method comprising:

receiving, from a first node that displays one or more medical images to a user, initial user interaction data pertaining to one or more user interactions with the one or more initially obtained medical images;

training a deep learning algorithm based at least in part on the initial user interaction data received from the node, wherein the initial user interaction data received from the node is weighted based on a rate of diagnostic accuracy of the user; and transmitting an instance of the trained deep learning algorithm to the first node and/or to one or more additional nodes, wherein at each respective node to which the instance of the trained deep learning algorithm is transmitted, the trained deep learning algorithm is applied to respective one or more subsequently obtained medical images in order to obtain a result.

2. The method of claim 1, wherein the initial user interaction data comprises one or more of:

(a) an actual or estimated portion of at least one of the one or more medical images that was focused upon by at least one user;

(b) at least one annotation on at least one of the one or more initially obtained medical images;

(c) a selection of one of more pixels associated with at least one of the one or more initially obtained medical images;

(d) an actual or estimated amount of time one or more users spent viewing one or more of the initially obtained medical images; and (e) a description of a patient condition and/or written or recorded audio diagnostic findings.

3. The method of claim 1, wherein the deep learning algorithm generates data models for detecting recurring patterns in medical images based on the initial user interaction data.

4. The method of claim 1, wherein the deep learning algorithm generates data models for detecting a localization in medical images based on the initial user interaction data.

5. The method of claim 4, wherein the localization comprises pixel or voxel coordinates.

6. The method of claim 1, wherein the deep learning algorithm generates a set of task flows.

7. The method of claim 6, wherein the rate of diagnostic accuracy of the user is low, and, in response, the deep learning algorithm modifies the set of task flows to provide the user with additional information.

8. The method of claim 1, wherein the instance of the deep learning algorithm records a medical history associated with a patient; and presents the medical history associated with the patient to the user.

9. The method of claim 1, further comprising receiving, from the first node and/or one or more additional nodes, subsequent user interaction data pertaining to one or more subsequently obtained medical images, wherein the subsequent user interaction data is used to modify the trained deep learning algorithm if it is determined that the subsequent user interaction data satisfies a predetermined threshold confidence level indicating that the trained deep learning algorithm should be modified.

10. The method of claim 9, wherein the predetermined threshold level requires a predetermined number of users to corroborate a particular detail.

11. The method of claim 9, wherein the predetermined threshold level is determined based on data pooled from a plurality of users.

12. The method of claim 9, further comprising running one or more data-mining algorithms on the subsequent user interaction data to determine the complexity of the subsequent user interaction data.

13. The method of claim 12, wherein the predetermined threshold level is a level of complexity of the subsequent user interaction data.

14. The method of claim 1, wherein the instance of the trained deep learning algorithm is a partial instance.

15. A dynamic self-learning medical image network system, comprising: a plurality of nodes; and
a central brain server configured to receive initial user interaction data from one or more nodes of the plurality, wherein the initial user interaction data pertains to one or more user interactions with one or more initially obtained medical images,
train a deep learning algorithm based at least in part on the initial user interaction data received from the node, wherein the initial user interaction data received from the node is weighted based on a rate of diagnostic accuracy of the user, and
transmit an instance of the trained deep learning algorithm to each node of the plurality,
wherein each node of the plurality is configured to apply the instance of the trained deep learning algorithm to one or more subsequently obtained medical images in order to obtain a result.

16. The system of claim 15, wherein the initial user interaction data comprises one or more of:
(a) an actual or estimated portion of at least one of the one or more medical images that was focused upon by at least one user;
(b) at least one annotation on at least one of the one or more initially obtained medical images;
(c) a selection of one of more pixels associated with at least one of the one or more initially obtained medical images;
(d) an actual or estimated amount of time one or more users spent viewing one or more of the initially obtained medical images; and
(e) a description of a patient condition and/or written or recorded audio diagnostic findings.

17. The system of claim 15, wherein at least one node of the plurality is a user interaction device.

18. The system of claim 15, wherein at least one node of the plurality is not a user interaction device.

19. The system of claim 18, wherein the at least one node is an intelligent workstation.

20. The system of claim 15, further comprising a central brain network, wherein the central brain server is communicatively coupled to the central brain network.

21. The system of claim 20, wherein the central brain server is one of a plurality of central brain servers.

* * * * *